US012678322B2

(12) United States Patent  (10) Patent No.: US 12,678,322 B2
Hamsch et al.  (45) Date of Patent: Jul. 14, 2026

(54) CONNECTION ROD FOR A TONGUE MANIPULATION SYSTEM

(71) Applicant: KONINKLIJKE PHILIPS N.V., Eindhoven (NL)

(72) Inventors: Matthias Hamsch, Aachen (DE); Pippinus Maarten Robertus Wortelboer, Eindhoven (NL); Chantal Nathalie Van Den Broek, Veldhoven (NL); Robert Charles, Hollis, NH (US); Asheesh Divetia, Los Gatos, CA (US); Barrett Hutto, Los Gatos, CA (US); Steve Woodard, Los Gatos, CA (US); Antonius Adrianus Petrus Schudelaro, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 820 days.

(21) Appl. No.: 15/504,670

(22) PCT Filed: Jul. 29, 2015

(86) PCT No.: PCT/IB2015/055710
§ 371 (c)(1),
(2) Date: Feb. 17, 2017

(87) PCT Pub. No.: WO2016/027185
PCT Pub. Date: Feb. 25, 2016

(65) Prior Publication Data
US 2018/0221042 A1   Aug. 9, 2018

Related U.S. Application Data

(60) Provisional application No. 62/040,096, filed on Aug. 21, 2014.

(51) Int. Cl.
*A61F 5/56* (2006.01)
*A61B 17/24* (2006.01)
(Continued)

(52) U.S. Cl.
CPC ................ *A61F 5/56* (2013.01); *A61B 17/24* (2013.01); *A61B 2017/00407* (2013.01);
(Continued)

(58) Field of Classification Search
CPC .... A61F 5/56; A61F 5/566; A61F 6/12; A61F 6/146; A61F 6/18; A61F 6/20;
(Continued)

(56) References Cited

U.S. PATENT DOCUMENTS

| | | | | |
|---|---|---|---|---|
| 4,614,187 | A | * | 9/1986 | Mulhollan ......... A61B 17/0469 606/144 |
| 6,210,415 | B1 | * | 4/2001 | Bester ................ A61B 17/1714 606/96 |
| 7,992,567 | B2 | | 8/2011 | Hirotsuka |
| 10,667,911 | B2 | | 6/2020 | Ketai |

(Continued)

FOREIGN PATENT DOCUMENTS

| | | |
|---|---|---|
| JP | 2008529608 A | 8/2008 |
| WO | 2007146338 A2 | 12/2007 |
| WO | 2010148246 A2 | 12/2010 |

*Primary Examiner* — Adam Baker
(74) *Attorney, Agent, or Firm* — Brynne J. Corcoran

(57) ABSTRACT

A connection rod for a tongue manipulation device system, the connection rod comprising: a first coupling part (307) configured to couple the distal end of the connection rod to a tongue advancer (305); a second coupling part (309) configured to couple the proximal end of the connection rod to an implant tool (101) or a removal tool (1601), wherein the connection rod is configured to transmit a tension or pulling force from the implant tool (101) or the removal tool (1601) to the tongue advancer (305) such that the tongue advancer is configured to be retracted within the implant tool (101) or removal tool (1601) respectively.

21 Claims, 21 Drawing Sheets

(51) Int. Cl.

| | |
|---|---|
| *A61B 17/00* | (2006.01) |
| *A61B 17/04* | (2006.01) |
| *A61B 90/00* | (2016.01) |

(52) U.S. Cl.

CPC ................. *A61B 2017/0409* (2013.01); *A61B 2017/0411* (2013.01); *A61B 2017/0437* (2013.01); *A61B 2017/248* (2013.01); *A61B 2090/064* (2016.02)

(58) Field of Classification Search

CPC .. A61F 6/208; A61F 6/225; A61F 6/24; A61F 6/14; A61F 6/142; A61B 2017/0409; A61B 2017/0411; A61B 2017/0412; A61B 2017/1205–12095; A61M 37/0069

USPC ........................................................ 128/848

See application file for complete search history.

(56) References Cited

U.S. PATENT DOCUMENTS

| | | | |
|---|---|---|---|
| 2002/0055767 | A1* | 5/2002 | Forde ........................ A61F 2/01 |
| | | | 623/1.11 |
| 2003/0208203 | A1 | 11/2003 | Lim et al. |
| 2007/0186933 | A1* | 8/2007 | Domingo ......... A61B 17/12022 |
| | | | 128/207.15 |
| 2008/0023012 | A1 | 1/2008 | Dineen et al. |
| 2008/0066769 | A1 | 3/2008 | Dineen et al. |
| 2008/0208265 | A1* | 8/2008 | Frazier .............. A61B 17/0401 |
| | | | 606/326 |
| 2011/0307021 | A1 | 12/2011 | Anderson et al. |
| 2011/0308529 | A1* | 12/2011 | Gillis ........................ A61F 2/00 |
| | | | 128/848 |
| 2012/0310280 | A1 | 12/2012 | Harrington |
| 2014/0102460 | A1 | 4/2014 | Catalano |
| 2018/0161142 | A1* | 6/2018 | Finger ................... A61B 17/50 |

* cited by examiner 113    105    103

107

109

111

101

309

403

401

407

405

307

413   411

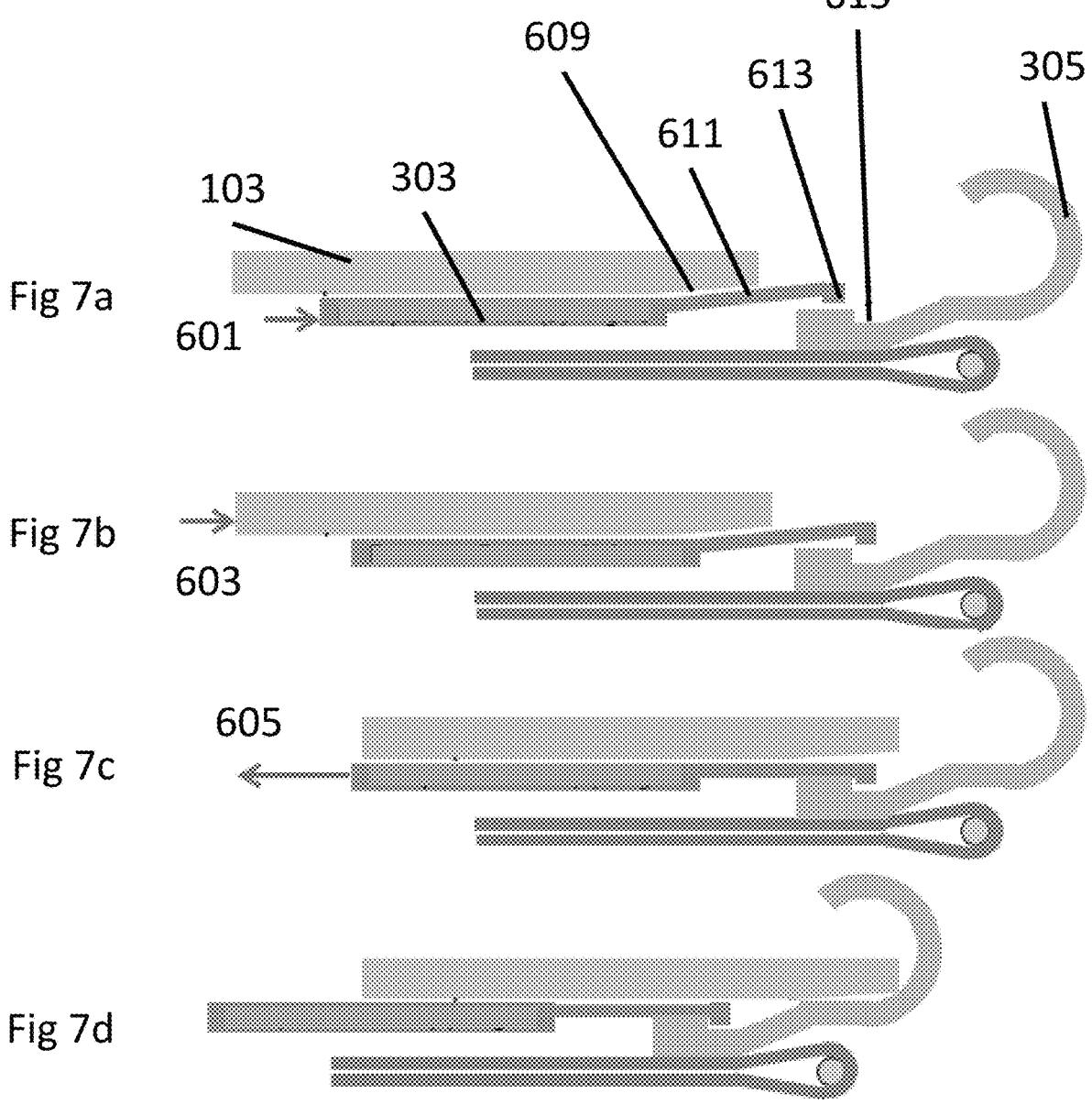

701

705

703

305

703

801

803

805

801

703

803 705 901

703

705

801

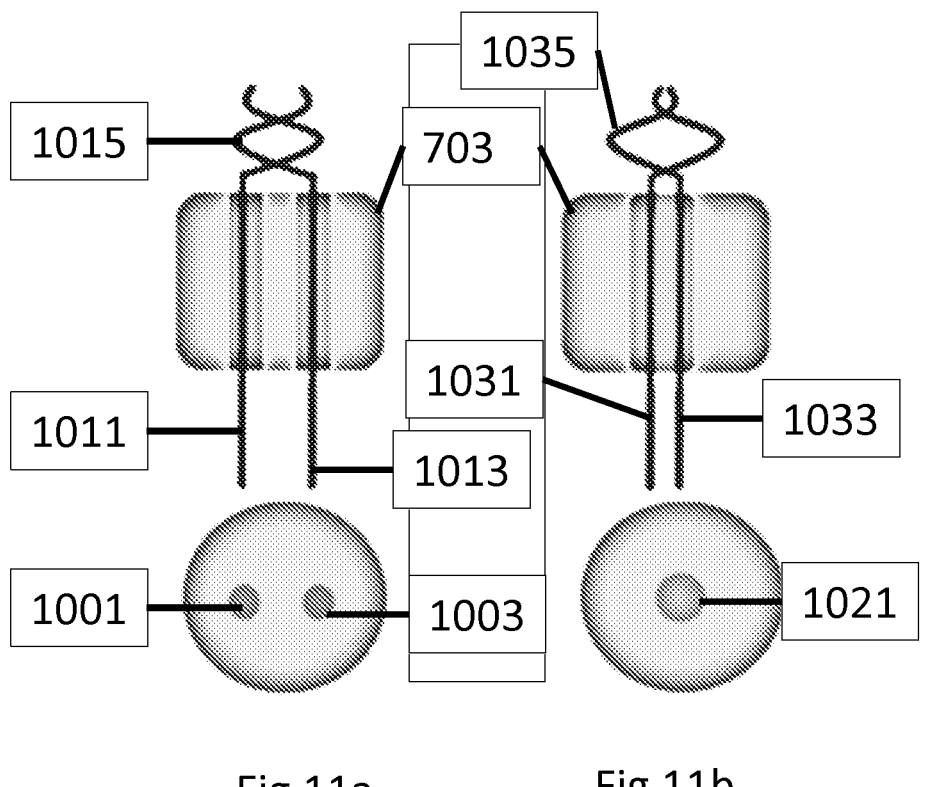
Fig 11a                    Fig 11b 1333    1335    1337

1336

1333

1336

1501

CONNECTION ROD FOR A TONGUE MANIPULATION SYSTEM

CROSS-REFERENCE TO PRIOR APPLICATIONS

This application is the U.S. National Phase application under 35 U.S.C. § 371 of International Application Serial No. PCT/IB2015/055710, filed on Jul. 29, 2015, which claims the benefit of U.S. Application Ser. No. 62/040,096, filed on Aug. 21, 2014. These applications are hereby incorporated by reference herein.

FIELD OF THE INVENTION

This invention relates to a tongue manipulation system, a tongue manipulation device, method and apparatus for tongue manipulation device implantation, tongue manipulation device adjustment and tongue manipulation device removal and particularly to a connection rod for a tongue manipulation system.

BACKGROUND OF THE INVENTION

It is known to use a tongue manipulation device to treat upper airway obstruction and sleep disordered breathing.

Respiratory disorders during sleep are recognized as a common problem with significant clinical consequences. Obstructive Sleep Apnoea (OSA) causes an intermittent cessation of airflow. When these obstructive episodes occur, an affected person will transiently arouse. Because these arousal episodes typically occur 10 to 60 times per night, sleep fragmentation occurs which produces excessive daytime sleepiness. Some patients with OSA experience over 100 transient arousal episodes per hour. OSA may also lead to cardiovascular and pulmonary disease.

Various approaches are known which aim to maintain the airway passage during sleep. Oral appliances aimed at changing the position of the soft palate, jaw or tongue are available, but patient discomfort has limited their use. Continuous Positive Airway Pressure (CPAP) devices are often used as first-line treatments for OSA. These devices use a sealed mask which produces airflow at a slightly elevated pressure and acts to maintain positive air pressure within the airway.

This disclosure relates to an approach by which a tongue manipulation device can be surgically applied to a patient. The complete device comprises three essential parts:

(i) a tongue advancer which is surgically placed inside the tongue;

(ii) a bone anchor which is typically attached to the mandible; and (iii) a tether line which fixes the tongue advancer to the bone anchor.

The bone anchor may feature a spool, enabling the surgeon to spool the tether into the bone anchor. This process is called adjustment and stabilizes the tongue as well as advances the tongue in the direction of the mandible (or prevents the tongue moving back), preventing blocking of the airway.

Generally, the implant is placed in the midline of the tongue at the base of the tongue and the device provides stabilization and advancement of the tongue base, so that the tongue can no longer move freely back. Instead, it is blocked by the tether line(s) connecting the bone anchor and tongue advancer.

SUMMARY OF THE INVENTION

The invention is defined by the claims.

According to a first aspect there is provided a connection rod for a tongue manipulation device system, the connection rod comprising: a first coupling part configured to couple the distal end of the connection rod to a tongue advancer; a second coupling part configured to couple the proximal end of the connection rod to an implant tool or a removal tool, wherein the connection rod is configured to transmit a tension or pulling force from the implant tool or the removal tool to the tongue advancer such that the tongue advancer is configured to be retracted within the implant tool or removal tool respectively.

In such a manner the connection rod in some embodiments is configured to transmit the pulling or tension forces required to retract the tongue advancer and in particular to straighten the tongue advancer fingers against the insert tool loading tube or the removal tool removal tube without applying the force to the tongue advancer tether and therefore enabling the tongue advancer tether to be optimised for the role of tongue manipulation rather than tongue advancer retraction and therefore be made with a thinner or more pliant material less likely to cause irritation to the patient.

The connection rod may be hollow at the distal end of the connection rod and configured to receive a tongue advancer tether. In such a manner the connection rod can in such embodiments locate and protect the tongue advancer tether during the operations of implantation and removal and therefore reduce the possibility of tether breakage or failure.

The first coupling part may comprise a screw thread configured to couple to an associated tongue advancer screw thread. The associated tongue advancer screw thread may be a variable diameter screw thread. In such embodiments the connection rod may achieve a positive coupling or connection may in some embodiments permit an oblique angle approach to the tongue advancer.

The screw thread may be an internal screw thread. In such embodiments the internal screw thread may be configured to couple to an associated external screw thread of the tongue advancer.

The screw thread may be an external screw thread. In such embodiments the external screw thread may be configured to couple to an associated internal screw thread of the tongue advancer. The screw thread may be a partially executed screw thread. In such embodiments the partially executed screw thread can be used to remove tissue from an already implanted tongue advancer.

The connection rod may comprise a plurality of slots cut into the distal end of the connection rod, the plurality of slots forming a plurality of tabs arranged with a helical pitch, the tabs configured to be bent to form the partially executed thread. Thus in some embodiments a partially executed screw thread can be formed from a connection rod without the need for substantial thread cutting or machining.

The first coupling part may comprise a clamp configured to clamp to the tongue advancer. In such embodiments the coupling can be performed without the need to rotate the connection rod.

The tongue advancer may comprise at least one groove to be clamped by the clamp. The tongue advancer may further comprise at least one ball shaped proximal end to be clamped by the clamp. In such embodiments the groove may provide a tactile feedback element indicating when a positive coupling has been achieved by the clamping elements within the groove or ball shaped feature in the tongue advancer.

The clamp may be an axisymmetric clamp. In such embodiments the clamping is capable of exerting a clamping force which is not directionally specific.

The clamp may comprise at least one clamping element comprising a clamping profiled inner surface element configured to clamp the tongue advancer. In such embodiments therefore the clamping profiled inner surface element clamps the tongue advancer to the connection rod and enables the transmission of the tension force to the tongue advancer without any slipping of the tongue advancer.

The clamping element may be radially biased and configured to pass over a proximal end of the tongue advancer in reaching a tongue advancer groove. In such embodiments the clamping elements, being radially biased, will deflect around any solid objects in the path of the connection rod. Thus for example the connection rod approaching the tongue advancer at an oblique angle can couple or connect to the tongue advancer as the clamping elements pass around the proximal end of the tongue advancer so that they can reach the appropriate clamping surface, such as the grooves in the tongue advancer.

The connection rod may be configured to be located within a hollow tube with a profiled inner surface such that as the hollow tube is moved in a distal direction over the connection rod, the profiled inner surface moves the clamping profiled inner surface element to clamp on a tongue advancer groove. In such embodiments the hollow tube provides, via the profiled inner surface a suitable radial inwards force pushing the clamping elements and the clamping profiled inner surface element into the tongue advancer groove and therefore clamping the tongue advancer securely.

The clamp may comprise a rounded distal end surface to allow the clamp to move over a tongue advancer proximal end. In such embodiments the clamping elements having rounded distal ends will deflect around any solid objects in the path of the connection rod. Thus for example the connection rod approaching the tongue advancer at an oblique angle can couple or connect to the tongue advancer as the clamping elements pass around the proximal end of the tongue advancer so that they can reach the appropriate clamping surface, such as the grooves in the tongue advancer.

The clamp may comprise a protrusion configured to contact a tongue advancer proximal end when the clamp is located in a position to clamp the tongue advancer. In such embodiments the protrusion acts as a stop to prevent the connection rod being pushed too far and pushing the tongue advancer away and can also act as a tactile indicator providing information to the operator of the tool, especially when the tool end is hidden or located within an object such as during the tongue advancer removal, that the connection rod or similar is located and a clamping can be performed.

The second coupling part may comprise a plurality of profiled grooves configured to interact with at least one hook or gearwheel to provide a ratchet mechanism for providing a tension or pulling force from the implant tool or removal tool. In such embodiments the profiled grooves may be configured to enable an easy retraction operation in a determined (inwards) direction for loading or retracting the tongue advancer.

The second coupling part may comprise a friction surface configured to interact with at least one clutch or gearwheel to provide a ratchet mechanism for providing a tension or pulling force from the implant tool or removal tool. In such embodiments the friction surface may be configured to enable an easy retraction operation in a determined (inwards) direction for loading or retracting the tongue advancer.

A connection rod proximal end may be configured to be profiled to assist insertion of the connection rod into the implant tool or the removal tool. In such embodiments the connection rod proximal end profile may direct the connection rod in towards the tool.

The connection rod may comprise: a removal sleeve comprising the first coupling part configured to couple the distal end of the connection rod to the tongue advancer; a removal adaptor comprising the second coupling part configured to couple the proximal end of the connection rod to the removal tool, wherein a proximal end of the removal sleeve is coupled to a distal end of the removal adaptor to form the connection rod.

According to a second aspect there is provided a tongue advancer, for a tongue manipulation system, the tongue advancer comprising: a connection rod coupling configured to couple the tongue advancer assembly to a distal end of the connection rod; at least one tongue advancer finger configured to be deployed to locate the tongue advancer.

The connection rod coupling may comprise at least one of: a screw thread configured to couple the tongue advancer to a connection rod by a connection rod screw thread; a groove configured to couple the tongue advancer to a connection rod by a connection rod clamping element; a ball-shaped proximal end configured to couple the tongue advancer to a connection rod by a connection rod clamping element.

According to a third aspect there is provided a tongue advancer implant tool for a tongue manipulation system comprising: a loading mechanism configured to enable the loading of a connection rod, wherein the loading mechanism is configured to co-operate with the coupling part of a proximal end of the connection rod; a propulsion element configured to be charged during the loading of the connection rod; a release mechanism configured to permit the propulsion element to propel the connection rod from the tongue advancer implant tool.

According to a fourth aspect there is provided a tongue advancer removal tool for a tongue manipulation system comprising: a loading mechanism configured to enable the loading of a connection rod comprising a removal adaptor coupled to a removal sleeve, wherein the loading mechanism is configured to couple the proximal end of the connection rod to the removal tool; a propulsion element configured to be charged during the loading of the removal sleeve; a release mechanism configured to permit the propulsion element to propel the removal sleeve from the tongue advancer removal tool.

According to a fifth aspect there is provided a method of retracting a tongue advancer within an implant tool or a removal tool comprising: coupling a distal end of a connection rod to the tongue advancer; coupling a proximal end of a connection rod to the implant tool or the removal tool, wherein applying a tension or pulling force to the tongue advancer via the connection rod by the implant tool or the removal tool, the connection rod transmitting the tension or pulling force such that the tongue advancer is retracted within the implant tool or a removal tool respectively.

The method may further comprise receiving a tongue advancer tether within a hollow at the distal end of the connection rod.

Coupling the distal end of a connection rod to the tongue advancer comprises screwing a screw thread at the distal end of the connection rod to an associated tongue advancer screw thread.

Screwing a screw thread at the distal end of the connection rod to an associated tongue advancer screw thread may be at an oblique angle where the associated tongue advancer screw thread is a variable diameter screw thread.

Screwing a screw thread at the distal end of the connection rod may further comprise removing tissue from the tongue advancer by the screw thread being a partially executed screw thread.

Generating a partially executed screw thread may comprise: cutting a plurality of slots into the distal end of the connection rod, the plurality of slots forming a plurality of tabs arranged with a helical pitch; bending the tabs to form the partially executed thread.

Coupling the distal end of a connection rod to the tongue advancer comprises clamping the tongue advancer.

Clamping the tongue advancer may comprise clamping at least one groove on the tongue advancer.

Clamping the tongue advancer may comprise axisymmetrically clamping the tongue advancer.

Clamping the tongue advancer may comprise: locating the connection rod within a hollow tube with a profiled inner surface; moving the connection rod in a distal direction over the tongue advancer such that at least one clamping profiled inner surface element is located adjacent a tongue advancer groove; moving the hollow tube in a distal direction over the connection rod, the profiled inner surface moving the at least one clamping profiled inner surface element to clamp on the tongue advancer groove.

Clamping the tongue advancer may comprise providing a clamping element rounded distal end surface to allow the clamp to move over a tongue advancer proximal end.

Clamping the tongue advancer may comprise providing a protrusion from the connecting element configured to contact a tongue advancer proximal end when the clamp is located in a position to clamp the tongue advancer.

Coupling at the proximal end of a connection rod to the implant tool or the removal tool may comprise providing at least one of: a plurality of profiled grooves configured to interact with at least one hook or gearwheel to provide a ratchet mechanism for providing a tension or pulling force from the implant tool; a friction surface configured to interact with at least one clutch or gearwheel to provide a ratchet mechanism for providing a tension or pulling force from the implant tool.

An implant assembly or a removal assembly for insertion into a respective implant tool or removal tool, the implant assembly or removal assembly may comprise: a connection rod as described herein; a tongue advancer.

BRIEF DESCRIPTION OF THE DRAWINGS

Examples of the invention will now be described in detail with reference to the accompanying drawings, in which:

FIGS. 7a-7d show schematically connection rod clamp coupling with the tongue advancer examples according to some embodiments;

FIGS. 11a-11b show further example tongue advancer to tongue advancer tether knotted couplings according to some embodiments;

DETAILED DESCRIPTION OF THE EMBODIMENTS

The embodiments as described herein relate to tongue manipulation devices having a tongue advancer for attachment to the tongue, a bone anchor typically for attachment to the mandible and a tether line which fixes the tongue advancer to the bone anchor and tools for the implantation, adjustment and removal of the tongue manipulation devices.

The concepts as described herein relate to tools specifically for the implantation and removal of the tongue advancer of the tongue manipulation devices. Specifically the concepts as described herein relate to a connection rod or tube suitable for coupling at a first end to the tongue advancer and at the opposite end to a suitably designed implantation or removal tool.

The tongue manipulation device approach consists of three main stages:

Implantation: In the implantation stage, the bone anchor, tongue advancer and tether are installed by minimally invasive surgery. The system is not 'loaded' or stressed at implantation to enable the healing process.

Adjustment: In the adjustment stage, the implanted apparatus is adjusted by spooling tether into the bone anchor after the healing process is completed. This advances the tongue in the direction of the mandible and prevents the tongue from moving back and blocking the airway.

Removal: In the optional removal stage the bone anchor, tongue advancer and tether are removed from the patient by minimally invasive surgery. This optional stage would be expected to be performed on a low percentage of treated patients and performed, for example, where the tongue manipulation system fails or is non-compliant.

To achieve a better understanding of the embodiments as described hereafter these three steps or stages are described in detail below with respect to the tools and methods for performing these stages.

Furthermore in order to simplify the understanding of the concepts described herein the operations or steps with respect to the implantation, adjustment and removal stages are described where possible in such a manner that tools are described or introduced in a sequential manner. It would be understood that in some embodiments of performing the operations or steps of each stage that it may be more logical to prepare all of the relevant tools or equipment prior to making a first incision (for example to reduce the time that the patient is under anaesthetic or is 'open') and as such the steps or operations as described herein are example step sequences only.

Figure 1:
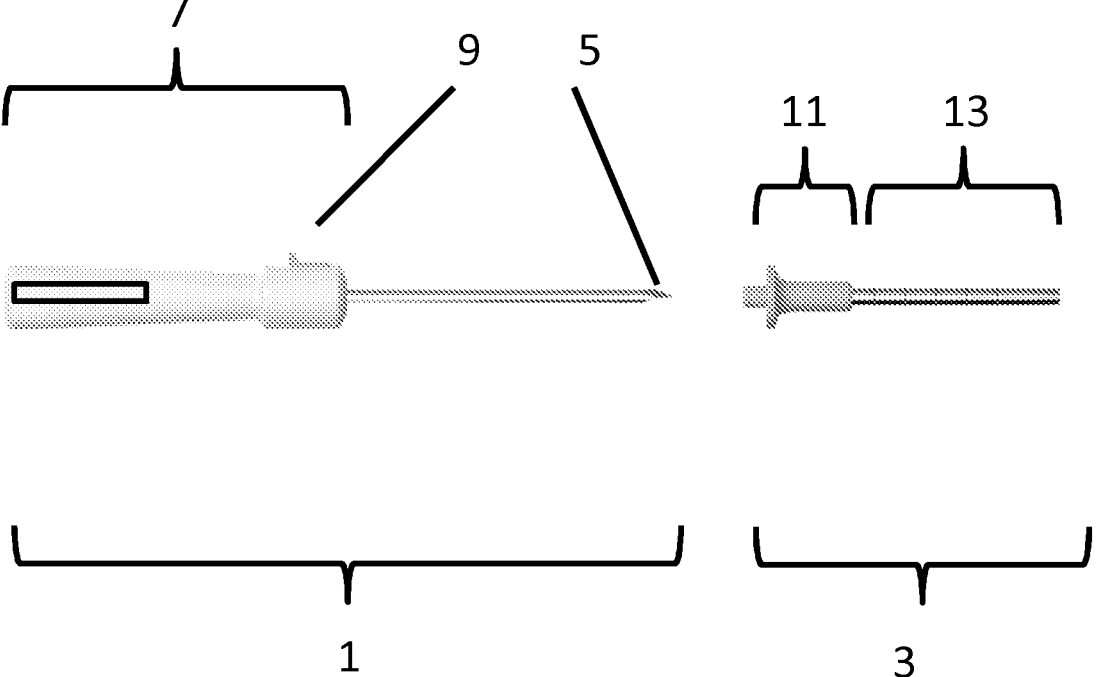
FIG. 1 shows schematically an example trocar tool with implant cannula with respect to some embodiments.
Figure 2:
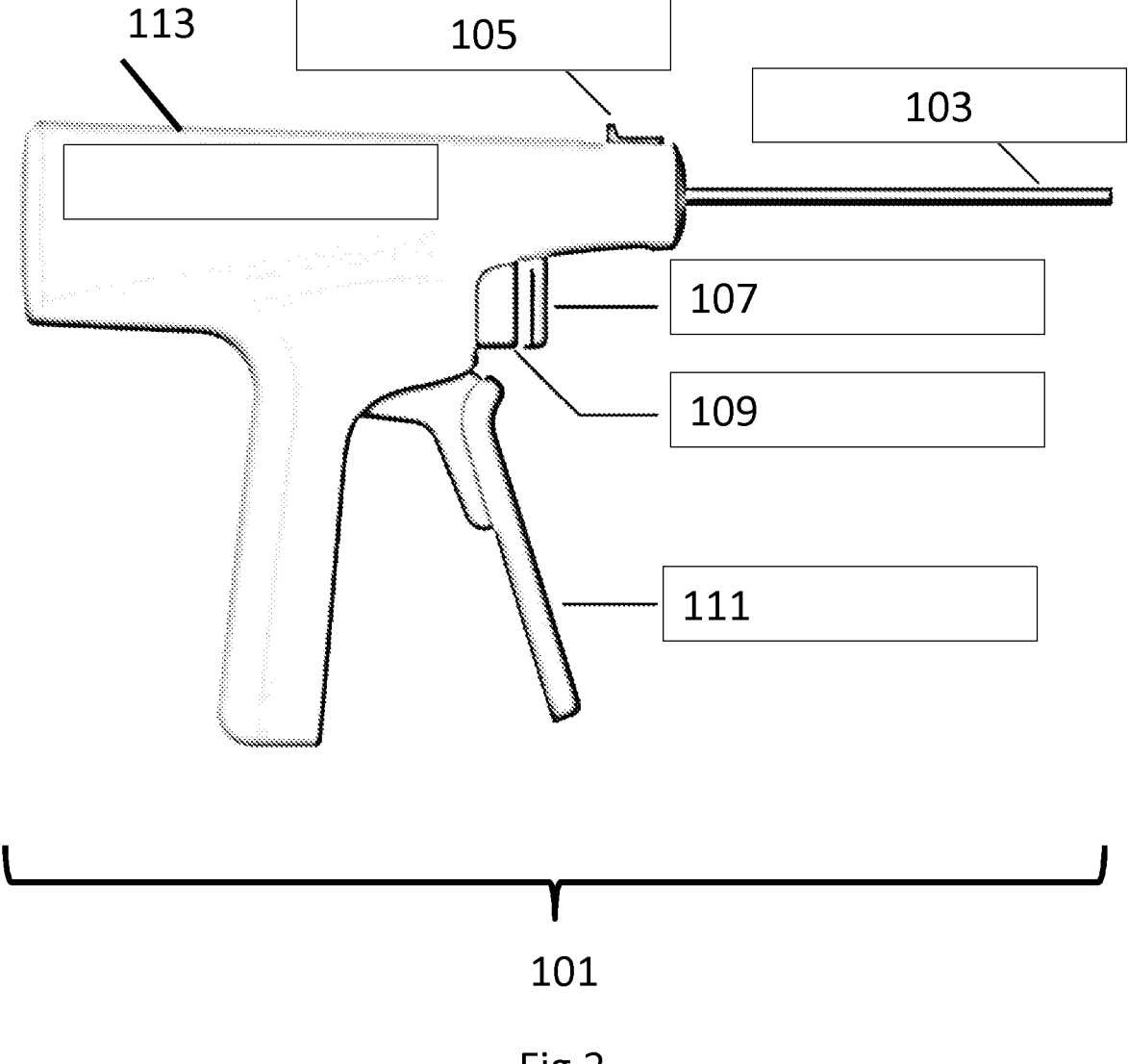
FIG. 2 shows schematically an implant tool with respect to some embodiments.
Figure 4:
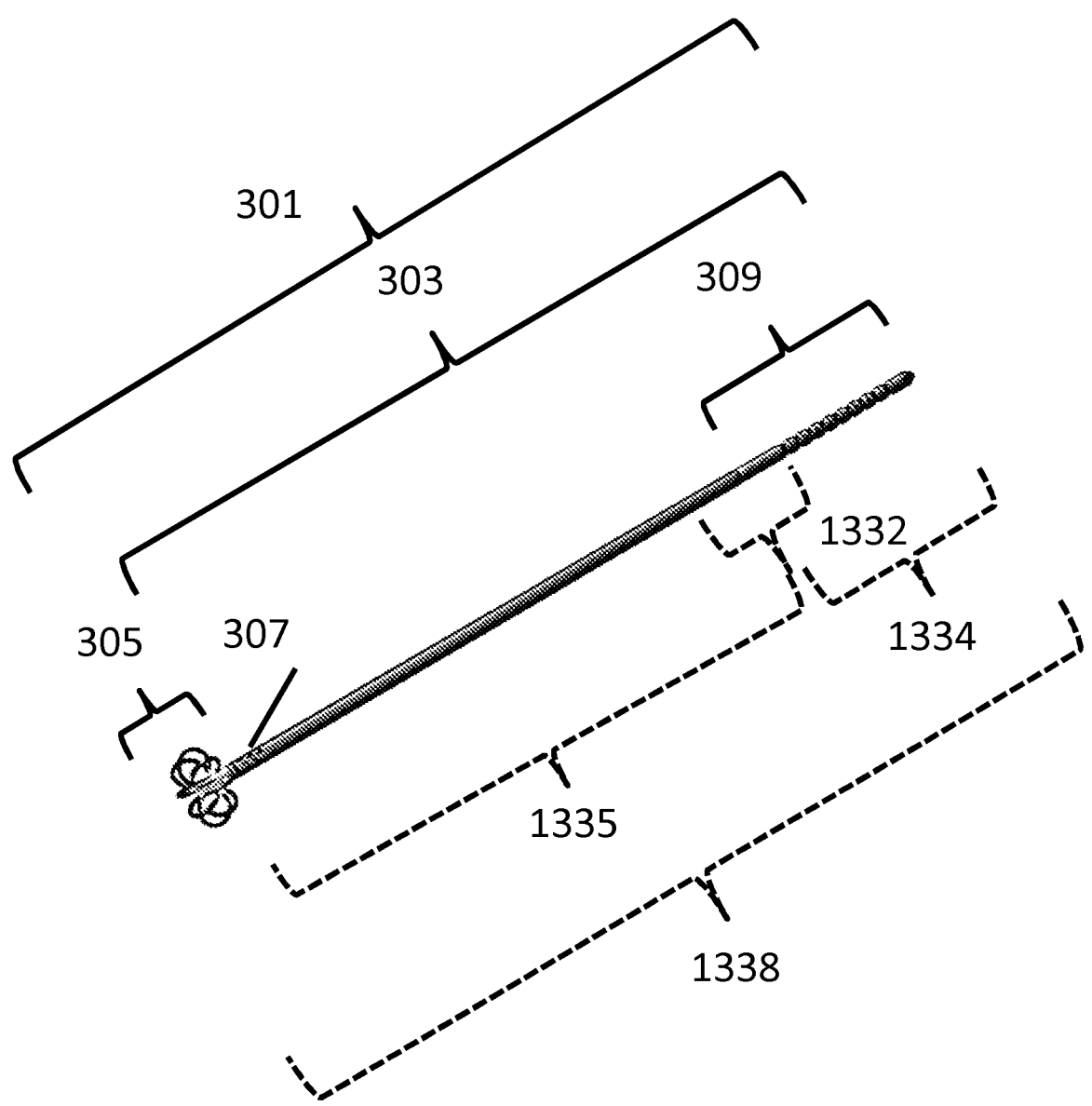
FIG. 4 shows schematically an implant/removal assembly with respect to some embodiments.
Figure 13:
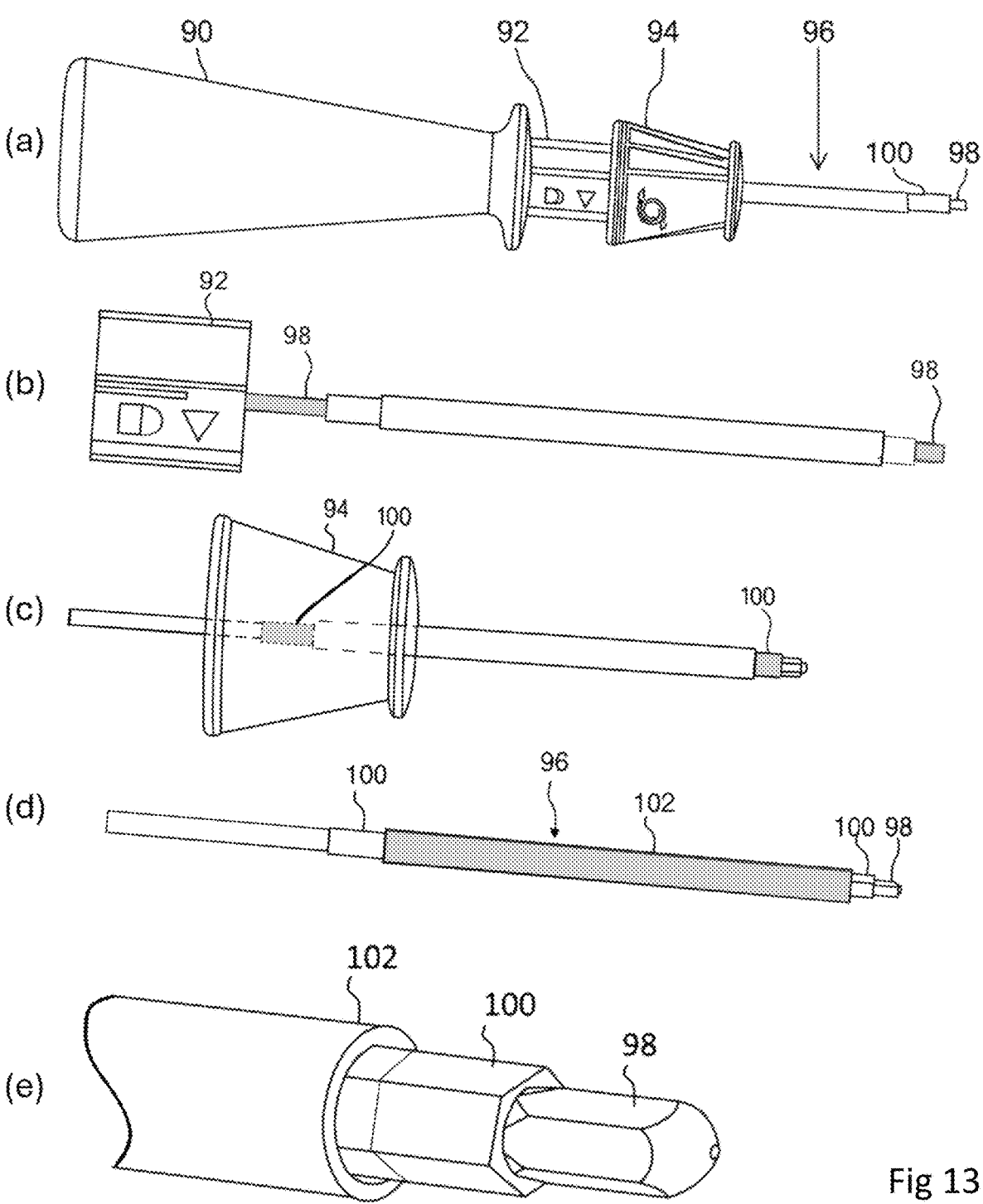
FIGS. 13a-13e show example adjustment tools according to some embodiments.

The implantation stage, in order to install the tongue advancer and the bone anchor, utilize the trocar tool 1 and the implant cannula 3 such as shown in FIG. 1, the implant tool 101 such as shown in FIG. 2, the implant assembly 301 such as shown in FIG. 4, the bone anchor, and the adjustment tool such as shown in FIG. 13.

In some embodiments the operator, such as the surgeon, prepares the patient's head for surgery.

In some embodiments the preparation of the patient can include the determination of the location of the bone anchor on the mandible, the incision at the desired location for the trocar preparing the mandible for the attachment of the bone anchor.

In some embodiments the preparation can include the location or potential location for the tongue advancer within the patient's tongue is located or determined. The potential location or position can in some embodiments be identified by palpation of the tongue surface. In some embodiments the preparation can further include the operator then places their index and middle fingers under the tongue to palpatate the floor of the mouth with the fraenulum between the two fingers to await the insertion of the channel insertion tool.

Figure 18:
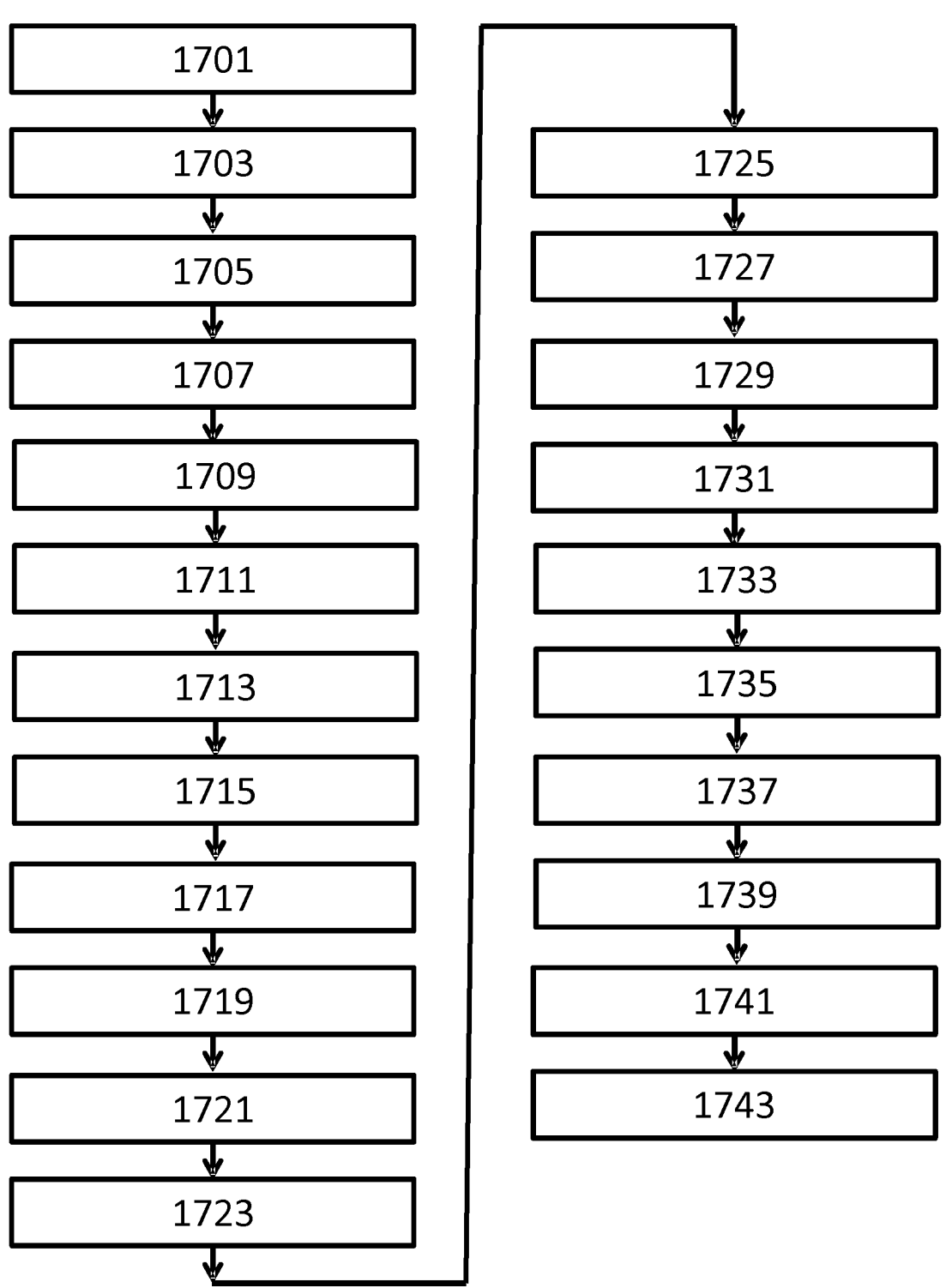
FIG. 18 shows a flow diagram of an example implant stage according to some embodiments.

The operation of preparing the patient is shown in FIG. 18 by step 1701.

With respect to FIG. 1 an example trocar tool and implant cannula 3 is shown. The example trocar tool as shown in FIG. 1 comprises a trocar 1 which in itself comprises a handle part 7 suitable for allowing the operator of the tool to grip the tool firmly and accurately. The trocar 1 furthermore comprises a trocar blade portion with a trocar tip 5 suitable for piercing and cutting a channel within soft tissue. The trocar blade portion and trocar tip 5 can be any suitable material such as surgical steel. The trocar 1 further comprises a coupling and/or latching section suitable for receiving an implant cannula 3. This can for example be an axis-symmetrical or axis-directional slot within the distal end of the trocar handle part 7. Furthermore the latching section can for example be implemented by an internal latching mechanism such as a lever with a profiled end configured to fit an associated profile on an implant cannula horn 11 when inserted into the trocar 1.

The trocar 1, and in some embodiments the trocar handle 7, furthermore comprises a cannula release button 9 or suitable latching release mechanism suitable for allowing the disconnection between the trocar 1 and the implant cannula 3.

The implant cannula 3 as shown in FIG. 1 comprises an implant cannula tube 13 and an implant cannula horn 11. The implant cannula tube 13 is a hollow tube which can be placed over the trocar blade portion and tip 5. The implant cannula tube 13 can be any suitable material, for example surgical steel, and is configured to provide a suitable stable channel within which the implantation of the implant can be performed.

The implant cannula horn 11 is configured to either fit over or to the proximal end of the implant cannula tube 13. In some embodiments the implant cannula horn is a moulded plastic shape configured to be received and be latched to the trocar 1 and specifically the trocar coupling and/or latching mechanism to produce a separable tool combination. The implant cannula horn 11 furthermore in some embodiments is configured to provide a suitable surface to grip when releasing or separating the trocar 1 from the cannula 3.

The first step or operation with respect to the implantation stage is in some embodiments to couple or connect the cannula 3 to the trocar 1 to form a channel insertion tool. It would be understood that in the embodiments as described herein the terms couple and coupling would be understood to define any suitable coupling, connecting or connection. Furthermore it would be understood that the terms connection and connecting would be understood to define any suitable connection or coupling. Similarly a decoupling would be understood to also define any suitable disconnection and vice versa.

The operation of coupling or connecting the cannula to the trocar tool is shown in FIG. 18 by step 1703.

In some embodiments the channel insertion tool, the trocar with the associated cannula attachment is inserted or introduced into the incision made earlier on the midline at an angle of approximately 90 degrees, directly into the genioglossus muscle of the floor of the mouth, until the sharp trocar end can be felt between the fingers. (The mucosa of the floor of the mouth must not be damaged).

The operation of introducing the trocar in the incision is shown in FIG. 18 by step 1705.

In some embodiments the channel insertion tool and the trocar is then orientated such that the trocar points to the base of the tongue and in particular the desired tongue advancer implant location.

The operation of orientating the trocar to the desired tongue advancer implant location is shown in FIG. 18 by step 1707.

The operator can then in some embodiments move their hand from the floor of the mouth to the dorsal surface of the tongue.

The operation of moving the hand to the dorsal surface of the tongue is shown in FIG. 18 by step 1709.

The operator can then in some embodiments advance of the trocar towards the base of the tongue aiming at the overlap of the horizontal and vertical parts of the tongue. In some embodiments the overlap of the horizontal and vertical parts of the tongue can be determined by palpation of the tongue surface with the hand in the mouth.

The operation of advancing the trocar to the base of the tongue is shown in FIG. 18 by step 1711.

The operator can then in some embodiments advance the trocar to approximately 1 cm away from the surface of the tongue. This distance can be determined or approximated by the palpating hand in the mouth. It would be understood that care must be taken in order that the surface of the tongue is not damaged.

The operation of advancing the trocar to the proximity of the surface of the tongue is shown in FIG. 18 by step 1713.

The cannula 3 is then separated from the trocar tool 1, for example by pressing the cannula release button 9 on the trocar tool 1. The trocar tool 1 is then removed from the cannula part 3 leaving the cannula part 3 and in particular the cannula tube 13 to form a stable channel within the patient.

The operation of separating and removing the cannula part 3 from the trocar tool 1 is shown in FIG. 18 by step 1713.

With respect to FIG. 2 an example implant (or implantation) tool 101 is shown. The implant tool 101 as shown in FIG. 2 comprises a body 113 incorporating a handle part. The body 113 can be manufactured or formed from any suitable material, for example from an injection moulded plastic. The body 113 can in some embodiments have other components mounted from it. For example as shown in FIG. 2 the body 113 is coupled or connected via an internal pivot point to a retraction lever 111. The retraction lever 111 in some embodiments as shown in FIG. 2 is configured to be operable by the use of at least one finger when the operator of the tool is holding the implant tool and can be formed from a moulded plastic part. The body 113 can in some embodiments be further coupled to a safety lever or cover 107 which is pivoted at a second pivot point within the body 113 and is configured to cover or prevent the accidental pressing of a release mechanism in the example of a release button or trigger lever 109. The body 113 can in some embodiments be further coupled or connected to an implant assembly release mechanism in the form of a release button or trigger 109.

The body 113 can in some embodiments further comprise a coupling and/or latching section suitable for receiving the implant cannula 3. This can for example be an axis-symmetrical or axis-directional slot within the distal end of the implantation handle 113. Furthermore the latching section can for example be implemented by an internal latching mechanism such as a lever with a profiled end configured to fit an associated profile on an implant cannula horn 11 when inserted onto the implant tool body 113. The body 113 can in some embodiments comprise a release or cannula release button 105 or suitable latching release mechanism suitable for allowing the decoupling or disconnection between the implant tool 101 and the implant cannula 3.

The body 113 in some embodiments further is coupled to a loading tube 103. The loading tool 103 is a hollow tube which projects at least partially out of the implant tool 101 and is configured to fit inside of the implant cannula when the implant cannula 3 is attached to the body of the implant tool 101.

Figures 3A, 3B:
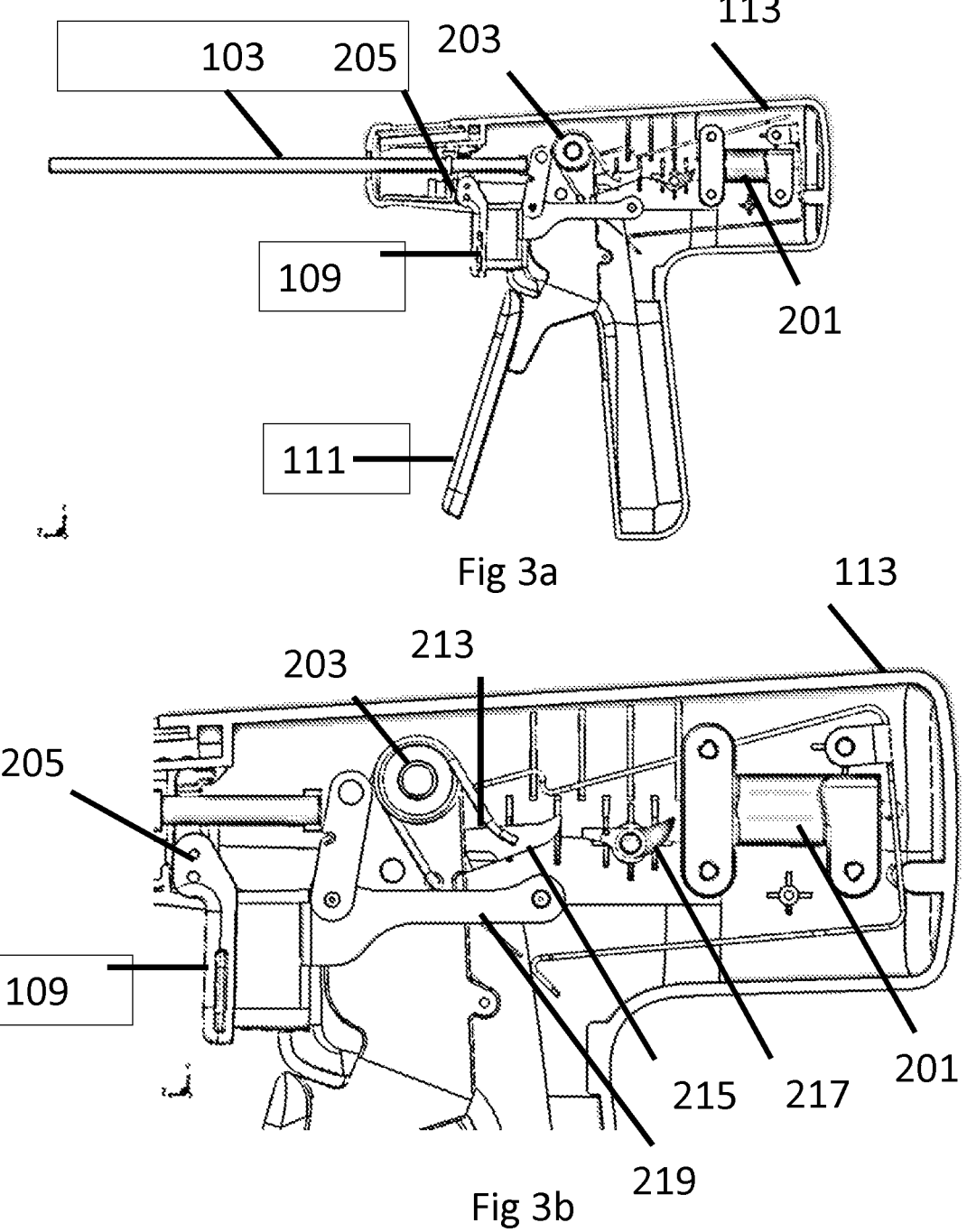
FIGS. 3a-3c shows schematically cross-section or cutaway views of an implant tool with respect to some embodiments.
Figure 3C:
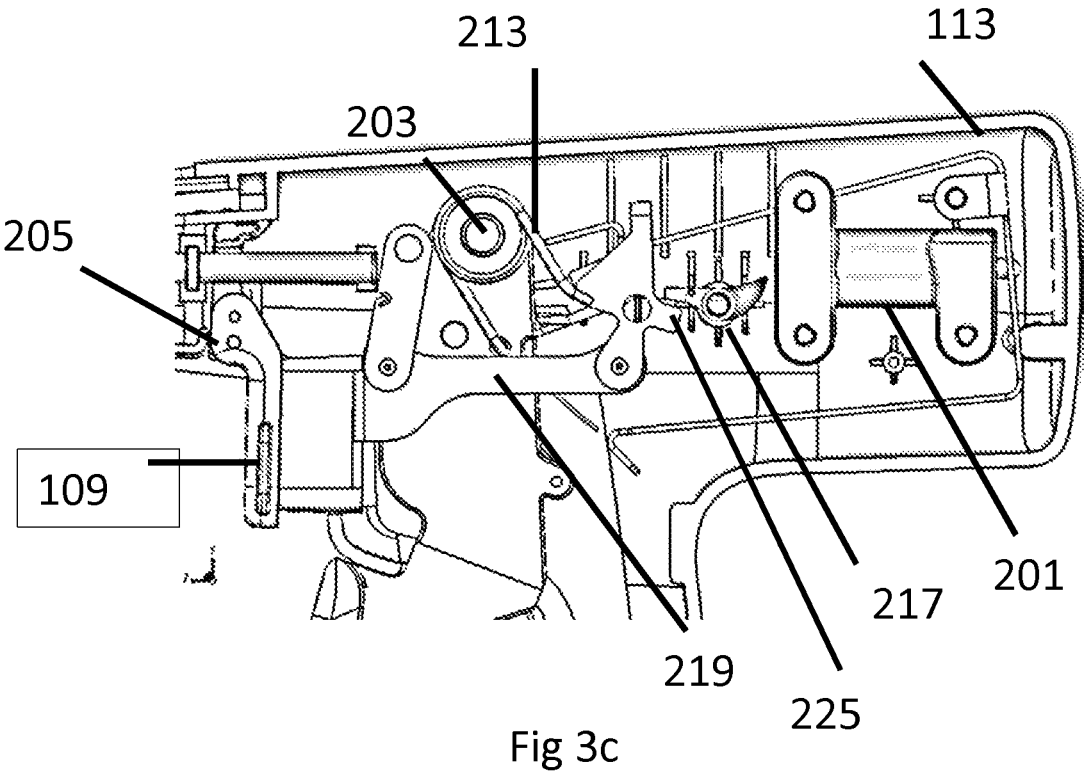

With respect to FIGS. 3a to 3c cross-sectional views of example implant tool 101 embodiments are shown. With respect to FIG. 3a a first cross-sectional or cut away view of the implant tool 101 is shown. In the example cross sectional views the internal latching mechanism, release or cannula release button 105 or suitable latching release mechanism and safety lever or cover 107 are not shown in these examples to assist the understanding of the mechanism as described herein and operated by the release mechanism and the implant tool retraction mechanism.

The implant tool cross-section shows the loading tube 103 which extends internally within the body 113 and can be configured to act as a guide with respect to an implant assembly as it is pushed/pulled into the implant tool. The cross sectional view of the implant tool 101 furthermore shows the release mechanism comprising the trigger lever 109, which is pivoted at the trigger pivot point 205, and the retraction lever mechanism comprising the retraction lever 111 and the retraction lever pivot point 203.

With respect to FIG. 3b a detail of the cross-sectional view of the implant tool as shown in the FIG. 3a is shown. The detail shows a loading mechanism comprising a first hook 215 coupled to the retraction lever mechanism and a second hook 217 which are both mounted such that they can pivot about respective points and hook or trap a ratchet groove feature on the implant assembly such that the implant assembly can move in one direction, an inwards direction, but is trapped and prevented from moving in an outwards direction. The loading mechanism in some embodiments therefore operates as a locking mechanism configured in a normal mode to permit the loading of an implant assembly in a direction inwards relative to the tool only. It would be understood that the term hook as used herein can define any suitable surface or profile enabling a hooking, gripping or catching of the implant assembly (or removal assembly).

The first hook 215 is coupled or connected to the retraction lever mechanism such that as the retraction lever is pulled towards the body 113 of the implant tool the first hook 215 moves in an inwards direction relative to the body 113. Furthermore the retraction mechanism comprises a biasing spring 213 configured to push the retraction lever away from the body 113 of the implant tool. In other words the user of the implant tool retraction mechanism has to overcome a small biasing or resting force to operate the retraction lever even when the retraction mechanism is not engaging an implant assembly.

Furthermore as shown in FIG. 3b the release mechanism comprising the trigger lever 109, which is pivoted at the trigger pivot point 205 is coupled to a mechanism 219 which affects or disengages the first hook 215 and the second hook 217 from the ratchet groove feature on the implant assembly. Furthermore the cross-sectional view of the implant tool body 113 shows an implant load spring 201 or propulsion element. The implant tool 101 is configured to receive the implant assembly and as the implant assembly is loaded (pulled/pushed) into the tool body to generate a suitable propulsive force (expulsive potential force). Although the following examples show a load spring it would be understood that in some embodiments any suitable propulsion element can be employed. Furthermore the propulsion element can in some embodiments be configured to be charged during the loading of the implant or removal assembly or charged at some point prior to the propelling of the implant or removal assembly. It would be understood that the release mechanism in some embodiments can indirectly enable the propulsion element to propel the implant or removal assembly from the implant or removal tool. The release button or mechanism can, for example, in some embodiments be configured to disable the normal mode of operation of the locking mechanism to permit the propulsion element to propel the implant assembly from the implant tool. However in some embodiments the release mechanism can be configured to directly enable the propulsion element to propel the implant or removal assembly from the implant or removal tool. For example in some embodiments the propulsion element can be latched or locked on being charged up and the release mechanism is then configured to unlock or unlatch the propulsion element directly.

With respect to FIG. 3c a detail cross-sectional view of a further embodiment implant tool. In this example the first hook 215 as shown in FIGS. 3a and 3b is replaced by a latching mechanism 225. The latching mechanism 225 is configured to operate in a similar manner to the first hook as it co-operates with the second hook as part of a locking mechanism but is also configured to operate on the second hook as part of the release mechanism to unlatch the implant assembly as the release button is pressed. The release mechanism in some embodiments is configured to disable the loading mechanism to permit the propulsion element to propel the implant assembly from the implant tool (or in some embodiments the removal assembly from the removal tool).

Although with respect to FIGS. 3a to 3c a latching or locking mechanism is shown employing hooks, it would be understood that any other suitable implementation of a loading mechanism, or a locking mechanism as part of a loading mechanism can be employed to enable the loading of an implant or removal assembly. Furthermore the loading mechanism can in some embodiments operate with respect to the connection rod and form a suitable locking or ratchet mechanism permitting in a first, normal or loading mode the connection rod (or the implant or removal assembly as discussed herein) to be loaded into the implant tool. For example in some embodiments the insertion tool comprises a suitable gearwheel to operate on the connection rod. As a further example in some embodiments the insertion tool comprises a suitable clutch mechanism and uses friction to couple to the connection rod (which has an associated friction surface formed by suitable means). In other words although the examples shown in FIGS. 3a, 3b, and 3c describe a hook based loading mechanism further configured to perform as a locking mechanism any suitable apparatus configured to permit the connection rod (or similarly in the removal tool the removal sleeve and removal adaptor) to be loaded in a manner similar to that described herein can be employed.

As described herein the implant tool is configured to receive via the loading tube 103 the implant assembly. With respect to FIG. 4 an example implant assembly 301 is shown. The implant assembly 301 can in some embodiments comprise a tongue advancer assembly (tongue advancer) 305 and a connection rod 303 (or ratchet or attachment sleeve). Furthermore FIG. 4 can show an example removal assembly 1338 comprising the tongue advancer 305, the removal sleeve 1335 and the removal adaptor 1334. The example removal sleeve can in some embodiments comprise at a proximal end a coupling 1332 for coupling the proximal end of the removal sleeve to a distal end of the removal adaptor 1334.

As shown in FIG. 4 the connection rod 303 comprises at the distal end a screw 307 or other suitable coupling means for coupling to the tongue advancer 305. Furthermore the connection rod 303 comprises at the proximal end a groove pattern 309 or other coupling means for coupling with the implant tool (and especially the loading mechanism) as the connection rod 303 is inserted into the implant tool. The connection rod 303 in some embodiments is at least partially hollow and configured to receive the tongue advancer 305 and the tongue advancer tether at least partially within itself in order that the tongue advancer 305 can be implanted according to the embodiments as described herein. The connection rod may be formed from a single piece of material, and be machined to form the screw 307 and/or groove pattern 309, or in some embodiments the connection rod 303 is formed from separately machined parts which are joined or fixed together.

In some embodiments the connection rod 303 is at least partially hollow enabling the tongue advancer tether to be guided during implantation (and furthermore the similar tube in the form of the removal sleeve can be employed within the connection tool allowing the tube to be guided along the tether to the tongue advancer during removal). The outer diameter of the connection rod is configured to fit the inner diameter of the implant tool loading tube 103 to permit the tongue advancer to be pulled into the tube. In such embodiments the tongue advancer fingers can be evenly straightened against the inner walls of the loading tube during the pulling in of the implant assembly to the implant tool and similarly enable an even unfolding of the anchor fingers during deployment.

As discussed below during removal surgery a channel can be created as the connection rod in the form of the removal sleeve approaches the tongue advancer. Furthermore the coupling or connection or docking of the tongue advancer and the connection rod (or removal sleeve) should in some embodiments be controlled such that the tongue advancer is first controlled or approached with very limited force to avoid pushing it away. The coupling or connection to the tongue advancer in some embodiments should be performed with limited (pushing) force to avoid displacement of the tongue advancer. Following the coupling of the tongue advancer to the connection rod or removal sleeve the tongue advancer should then be securely coupled to the rod which is pulled into the implant loading tube (or removal tool removal tube) by applying a pulling force.

Figures 5A, 5B:
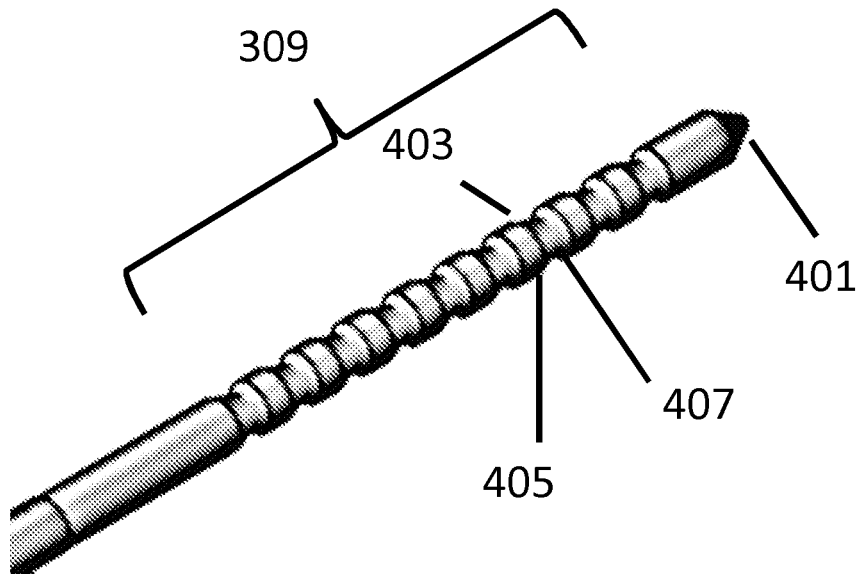
FIGS. 5a-5b show schematically details of the connection rod part of the implant/removal assembly shown in FIG. 4 with respect to some embodiments.

With respect to FIG. 5a a detail of the connection rod groove pattern 309 is shown. The groove pattern is shown having a series of grooves 403 which may be machined, pressed, moulded or otherwise formed. The grooves 403 comprise a variable profile or asymmetrical groove pattern where the proximal end 407 of the groove 403 is thinner than the distal end 405 of the groove 403. FIG. 5a furthermore shows an example connection rod having a tapered proximal end to assist insertion into the implant tool.

The groove pattern 309 is such that the grooves co-operate with the hooks 215, 217 or lever and hook 225, 217 combinations within the implant tool 101 such that the hooks allow the connection rod to move into the implant tool as the hooks slide over the distal end 405 of the groove 403 but latch to the proximal end 407 of each groove 403 to prevent the implant assembly comprising the connection rod from exiting the implant tool while the hooks and/or hook and lever are in operation (in other words when the loading mechanism is operating in a normal mode).

In such a manner a ratchet or locking mechanism is formed between the connection rod and the implant tool. Although in the example shown herein the ratchet mechanism is formed from a groove and hook/lever combination it would be understood that in some embodiments any other suitable ratchet or locking mechanism can be employed. For example in some embodiments the connection rod 303 has at the proximal end a friction surface which is gripped within the implant tool by a suitable friction wheel. The implant tool friction wheel in such embodiments may employ a one-way slipping clutch or a brake mechanism which in a first loading mode allows the connection rod to be inserted by allowing motion into the implant tool but prevents the connection rod exiting or leaving the implant tool.

With respect to FIG. 5b a detail of the connection rod screw 307 is shown. The connection rod screw 307 is formed in some embodiments by a pitch 413 defined slots 411, which in some embodiments is a asymmetric C or U slot, cut into the connection rod and which form tab material parts which can be bent or pressed either outwards (to form an external screw thread) or inwards (to form an internal screw thread). The pressed slots form a discontinuous screw thread which can be configured to couple to a suitable screw tread on the tongue advancer. Although the coupling is shown as a discontinuous screw thread it would be understood that the screw thread can be a continuous screw thread.

It would be understood that the screw thread coupling or interface can in some embodiments comprise one or both screw threads having a continuous or only partly executed thread. For example a partial execution such as shown in FIG. 5*b* may offer larger number of sharp edges to enable the scraping off of tissue from the associated other screw thread (such as in the case of removal) and therefore leave space to absorb any tissue scraped or left while attempting to attach the screw threads together.

Figure 6A:
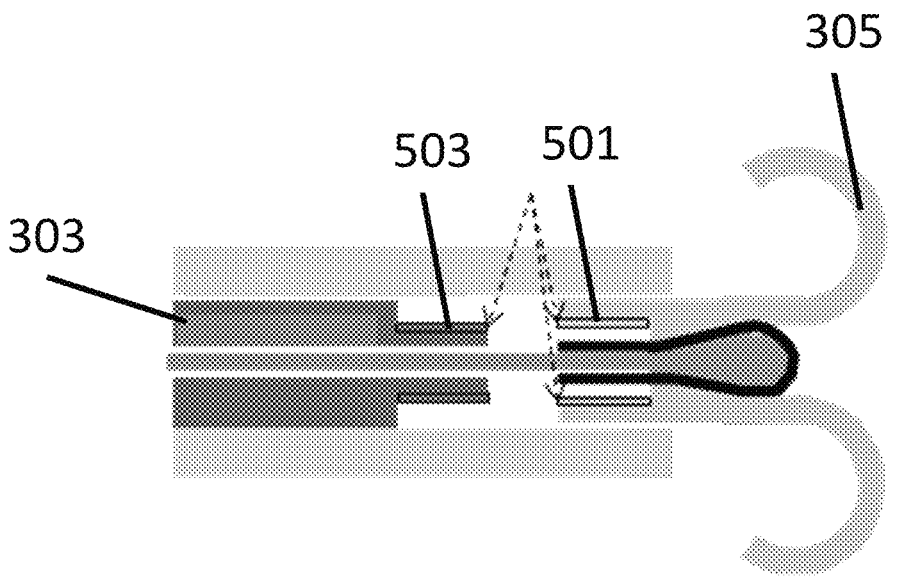
FIGS. 6a-6b show schematically connection rod screw coupling with the tongue advancer examples according to some embodiments.
Figure 6B:
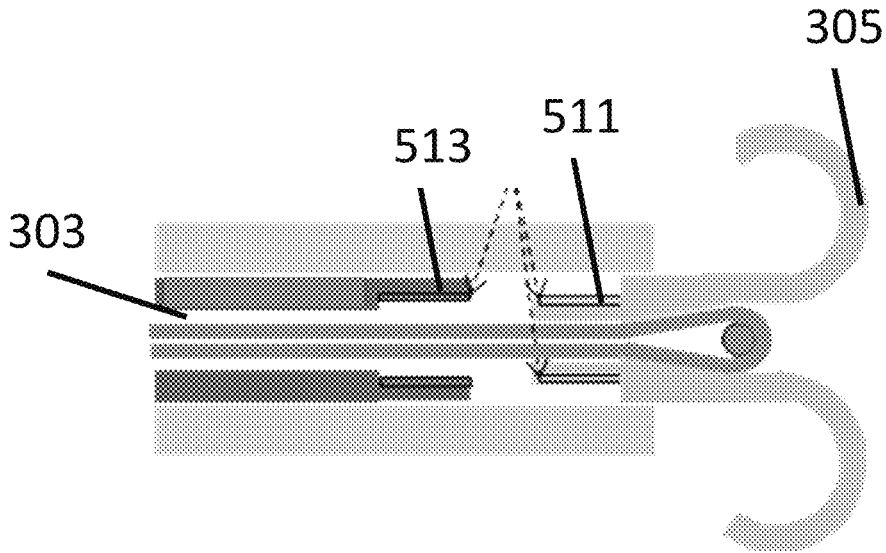

With respect to FIGS. 6*a* and 6*b* example screw couplings or interface configurations between the connection rod 303 and the tongue advancer 305 are shown. The example shown in FIG. 6*a* for example employs a screw couplings or interface configuration wherein the tongue advancer 305 comprises an internal screw thread 501 and the connection rod 303 comprises an external screw thread 503. Whereas with respect to the example shown in FIG. 6*b* the tongue advancer 305 comprises an external screw thread 511 and the connection rod 303 comprises an external screw thread 513

In some embodiments one or both of the screw threads on the tongue advancer 305 or the connection rod 303 may have a constant diameter. However in some embodiments the screw threads can have a variable diameter. A variable diameter screw thread should for example permit the approaching of the screw thread from a slightly off axis path (or in other words an oblique angle) and still enable the coupling to the associated opposing screw thread.

In some embodiments the connection rod and/or tongue advancer can also be configured to comprise a coupling or connector pair which is at least partially a ball or socket shaped coupling. For example in some embodiments one of the connection rod and/or tongue advancer comprises a ball shaped coupling (possibly partly flattened to provide a gripping surface). The other of the connection rod or tongue advancer then comprises a corresponding socket coupling (possibly including a gripping element). In such embodiments an off axis (oblique angled) approach would still enable the coupling of the connection rod and the tongue advancer.

It would be understood that in some embodiments the interface or coupling between the connection rod and the tongue advancer can be any suitable interface or coupling. For example the interface is an axisymmetric clamping means rather than a screw interface.

With respect to FIGS. 7*a* to 7*d* a suitable axisymmetric clamping interface is shown.

In the example shown in FIG. 7*a* the connection rod 303, which is located at least partially within the loading tube 103 of the implant tool 101, comprises a first coupling arm or element 611. The coupling element 611 in some embodiments is configured with a profile having a profiled surface or clamp 613 suitable for locating a groove 615 on the tongue advancer 305.

Although the following examples show a single groove 615 and single profiled surface element or clamp 613 it would be understood that in some embodiments the interface comprises more than one groove and in some embodiments the coupling element 611 comprises more than one profiled surface element or clamp suitable for interfacing with the more than one groove.

Furthermore in some embodiments the coupling element is at rest or in normal operation biased in a direction away from the axial centre. Furthermore in such embodiments the loading tube 103 of the implant tool 101 (or any tube within which the connection rod is operating) may comprise a profile 609 which opens up in the tube's distal direction. In other words the tube internal diameter or radius increases towards the opening of the tube. This can for example, as shown in FIGS. 7*a* to 7*d*, be achieved by progressively thinning the tube wall thickness along the inside of the tube to the end of the tube.

Thus as the connection rod is moved in a outwards or distal motion as shown by arrow 601 the coupling element 611 opens up the clamping element 613 because of the profile 609 of the loading tube and enables the clamping element 613 to pass over the end of the tongue advancer 305 until the clamping element 613 is located substantially adjacent the tongue advancer 305 groove 615 such as shown in FIG. 7*b*.

With respect to FIG. 7*b* the loading tube 103 (or outer tube) can be moved in an outward or distal direction, shown by the arrow 603, relative to the connection rod 303 such that the clamping element 613 is pushed inwards by the profiling 609 of the loading tube causing the clamping element 613 to lock or latch the tongue advancer 305 by the groove 615 such as shown in FIG. 7*c*.

With respect to FIG. 7*c* the connection rod 303 is then moved in an inwards or proximal direction. The tongue advancer 305 which is clamped by the clamping elements 613 within the groove 615 is thus moved inwards or proximally such that the tongue advancer 305 can be pulled at least partially within a loading tube (or other suitable tube) such as shown in FIG. 7*d*.

In other words in some embodiments connection rod can be configured to employ clamps as coupling elements. The clamps can in some embodiments be positioned around the tongue advancer shaft. This manoeuvre can be performed with a mild force since the clamps do not need to snap immediately into position or withstand high forces. The outer tube or tool tube (which can be for example the loading tube part of the implant tool, or the cannula of the removal tool) can be configured to slide over the connection rod clamps and lock the clamps when it is positioned over the distal end of the clamps. This locking process provides the stability to withstand high pulling forces.

In some embodiments the groove 615 of the tongue advancer 305 is configured to run over the complete circumference of the tongue advancer, however it would be understood that in some embodiments the groove is discontinuously distributed about the circumference of the tongue advancer. In some embodiments the groove 615 is configured to have a clear blocking edge at the proximal side and sufficient tolerance at the distal side.

In some embodiments the clamping elements have profiled or rounded ends to further assist the clamping elements to pass over the proximal end of the tongue advancer in the process of locating the groove 615.

In some embodiments the connection rod can be configured to have a protrusion inside the rod which contacts the tongue advancer proximal end when the clamping elements 613 pass the tongue advancer groove 615. In such embodiments the contact provides tactile feedback to the user or operator of the tool (such as the implant or removal tool) that the clamping elements are at the correct position to start gripping by shifting the outer loading tube over the connection rod.

In some embodiments the connection rod is configured to be rotated in order to sense the contact between the connection rod clamping elements 613 and the tongue advancer. Furthermore the rotation of the connection rod clamping elements 613 can in some embodiments have the additional effect of being able to scrape tissue overgrowth from the tongue advancer.

In some implements the proximal end of the tongue advancer is configured to have a ball shaped configuration or arrangement which allows the sliding of the connection rod clamps over the tongue advancer proximal end independent of the angle between the connection rod and the tongue advancer.

Figure 8:
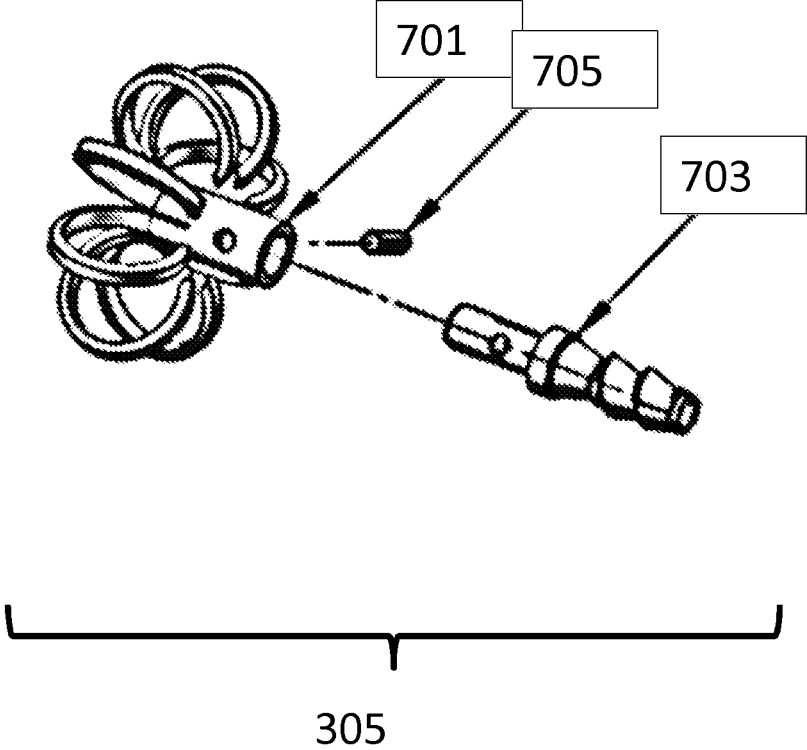
FIG. 8 shows an example tongue advancer according to some embodiments.

With respect to FIG. 8 an example tongue advancer assembly 305 according to some embodiments is shown. The tongue advancer assembly 305 (or tissue or tongue anchor) is configured to provide an anchoring function to the surrounding muscle tissue as well as a reliable connection to the bone anchor via a tether. Furthermore, the tongue advancer assembly 305 requires a suitable interface for connection to the implant tool (and furthermore to the removal tool) able to withstand high tension or pulling forces required to enable tongue advancer finger straightening and to therefore enable minimally invasive implantation and removal.

In the example shown in FIG. 8 the tongue advancer assembly 305 comprises a main or tongue advancer part 701. In such embodiments it is beneficial to manufacture the main part 220 of the tongue advancer assembly 305 including the tongue advancer fingers from a material such as Nitinol which has the required mechanical characteristics in terms of bio implant performance and resilience of the anchor or finger parts. The tongue advancer fingers as part of the tongue advancer part 701 of the tongue advancer 305 can be a rod, tube or similar object shape with fingers which at rest fold about themselves.

However machining of Nitinol or similar materials by standard production processes is difficult as these materials produce significant tool wear which therefore makes the production process expensive and requires higher efforts for controlling machines and process. Furthermore the fixation of the tether to the Nitinol or similar material is typically difficult at fixation in that weld or glue bond quality is usually poor.

In such embodiments as described herein the tongue advancer thus comprises a core mount 703 which is manufactured or constructed from different materials which do not require the feature of high elasticity. Furthermore in some embodiments the core mount 703 is fixed or coupled to the tongue advancer part 701 via a suitable coupling. For example the coupling shown in FIG. 8 is a round connecting pin 705 which is configured to pass through suitable cooperating holes within the tongue advancer part 701 and within the core element 703. Although the coupling between the core mount 703 and the tongue advancer part 701 is shown fixed by the round connecting pin 705 it would be understood that any other suitable fixing or coupling could be implemented in other embodiments.

Furthermore the tongue advancer 305, and specifically in the example shown in FIG. 8 the core mount 703, comprises a suitable connection rod interface in the form of a variable diameter external screw thread. However it would be understood that any suitable coupling or interface (such as external or internal screw thread such as shown in FIGS. 6a and 6b), ball, socket or groove (such as shown with respect to FIGS. 7a to 7d) can be employed in some embodiments.

Figure 9:
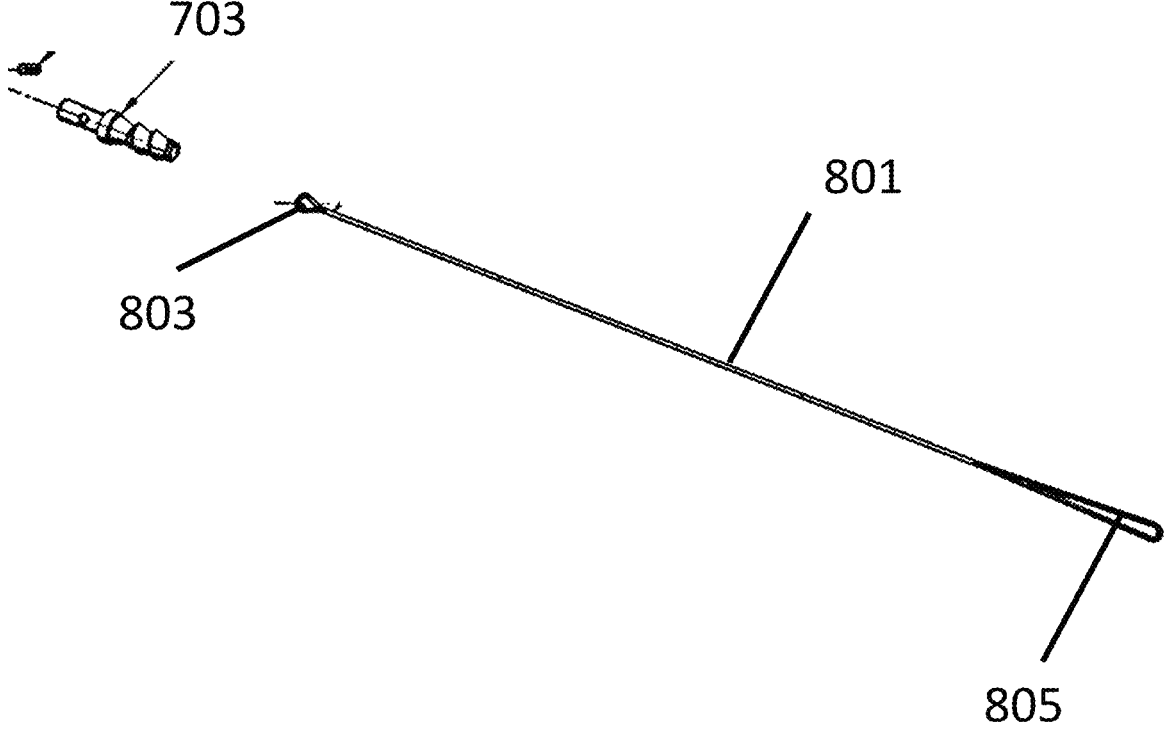
FIG. 9 shows an example tongue advancer coupling to a tongue advancer tether according to some embodiments.

With respect to FIG. 9 the core mount (or core element) 703 and the tongue advancer tether 801 is shown in further detail. The core element 703 in some embodiments comprises a hollow tube like structure through which can pass a first loop 803 of the tether 801. The first loop 803 of the tether 801 can furthermore be fixed in position relative to the tongue advancer assembly 305 in some embodiments by the connecting pin 705 which is used to fix or couple the core element 703 to the tongue advancer part 701. In other words the tether 801 is fixed by the pin, which has the advantage that by design the tether does not come into contact with sharp objects or edges.

Although in the example shown herein the tether 801 is formed from a single central element with first loop 803 configured to attach to the tongue advancer and the second loop 805 for coupling with the bone anchor it would be understood that any suitable tether arrangement can be implemented or employed, such as for example a complete loop tether.

Figure 10A:
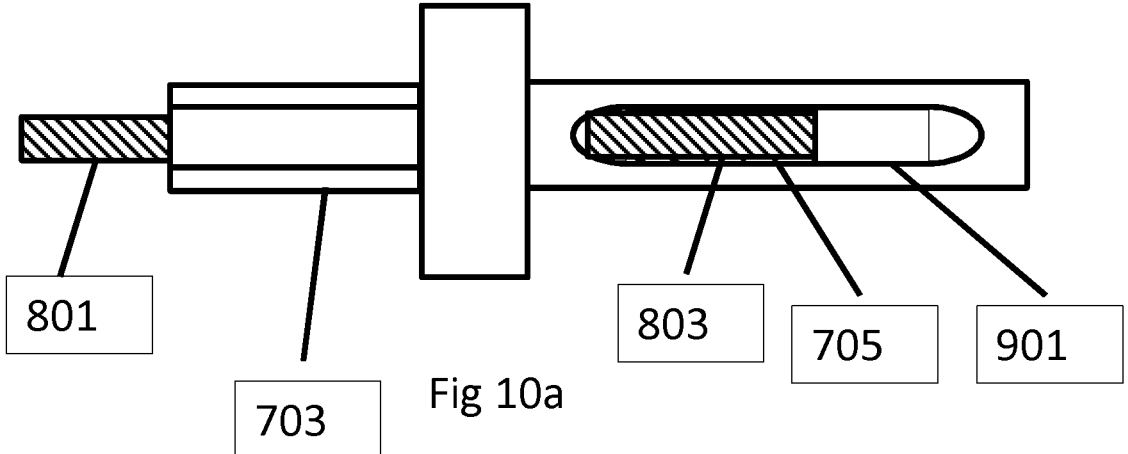
FIGS. 10a-10b show further example tongue advancer to tongue advancer tether couplings according to some embodiments.
Figure 10B:
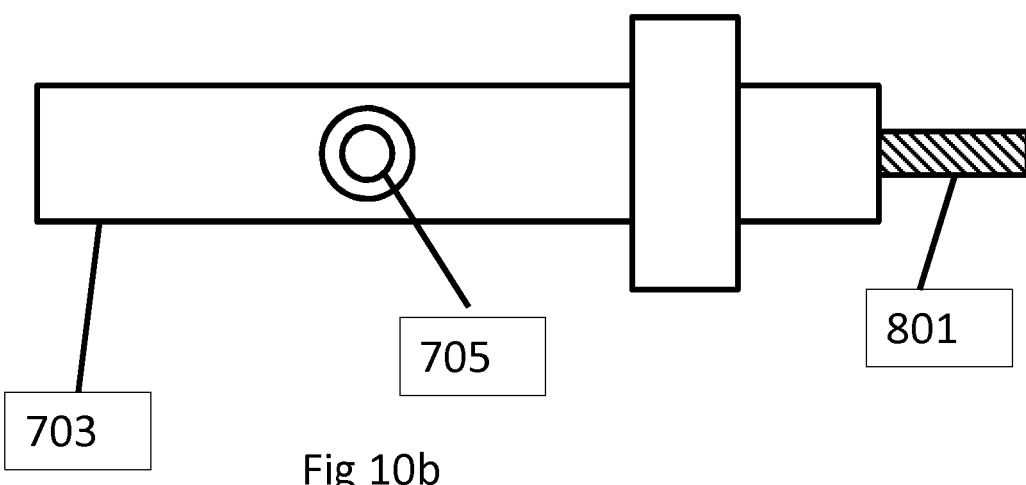

With respect to FIGS. 10a and 10b example core mounts 703 according to some embodiments are shown in further detail. With respect to FIG. 10a a first example core mount 703 is shown comprising an elongated slit 901 along the body of the core mount and at substantially 90° from the axis of the round pin 705. The elongated slit 901 permits the visual inspection of the mounting or fixing of the tether 801 and the tether first loop 803 and the pin 705 as the tether can be inspected visually for correct placement.

The pin 705 coupling the tongue advancer part 701 to the core mount 703 overcomes the need to weld the Nitinol or similar material of the anchor part 701 with the different and machineable material of the core mount 703. The pin 705 can in some embodiments reside in a hole of the core mount 703 and is fixed to the core mount by a shape or form fit. For example the form fit may be a round pin and round hole. The hole within the core mount 703 can be used in some embodiments to hold the pin 705 and in addition to the fixation in the core mount the pin can also reside in two holes of the Nitinol tube wall of the anchor part 701. In some embodiments the main stabilisation against the push and pull forces is by form fit also. In order to prevent the pin from working loose in some embodiments it is can be welded to the core mount 703 tube wall such as shown in FIG. 10b. In some embodiments the pin is manufactured from Nitinol and welded to the anchor part wall. With respect to FIG. 10b a further example of a core mount 703 is shown. In this example the tether 801 passes into the core mount 703 and around a welded pin 703.

Although the tether 801 is shown herein fixed to the core mount 703 by the connection pin 705 it would be understood that any other suitable fixing could be employed. For example with respect to FIGS. 11a and 11b knotted tether fixation embodiments are shown. With respect to FIG. 11a a core mount 703 is shown having two interior channels 1001, 1003 through which a separate line 1011 1013 of the tether loop is passed and knotted to form a tether knot 1015 which secures the tether relative to the core mount 703. With respect to FIG. 11b the core mount 703 is shown having a single channel 1021 through which both lines 1031, 1033 of the tether pass and which are knotted to form the tether knot 1035. It would be understood that in the single channel 1021 example that the knot 1035 has to be large enough to prevent slippage or slipping through the channel.

In some embodiments only one pin 705 is used to couple or connect the tether to the core mount 703 and to couple or connect the core mount 703 to the tongue advancer part 701. In such embodiments the pin therefore fulfils two functional roles. In some embodiments of the pin 705 is welded to the core mount 703 and coupled to the anchor part (Nitinol tube) by shape fit only. In such embodiments the pin 705 is manufactured from the same material as the core mount 703 to reduce the possibility of a weld failure.

The core mount 703 in some embodiments can be formed from a single part or multiple parts that are connected together. The core mount can for example be manufactured from a suitable material such as stainless steel, titanium, durable plastic, or other biocompatible material.

In some embodiments of the core mount is mounted completely or only partially inside the anchor part. In some embodiments the core mount is mounted outside the anchor part and thus encloses the tongue advancer part shaft.

In some embodiments as described herein the connection rod or tube is configured to be coupled or connected to the proximal end of the tongue advancer to produce an implant assembly. In such embodiments the coupling or connection between the tongue advancer and the connection rod enables a high pulling or tension force coupling between the tongue advancer and the connection rod and therefore enables the tether to be substantially thinner and more flexible than current designs which require the tension force to be carried by at least one tongue advancer tether.

The implant assembly, comprising the connection rod and the tongue advancer, can then be, in some embodiments, inserted from the proximal end the connection rod into the implant tool 101.

Figure 12A:
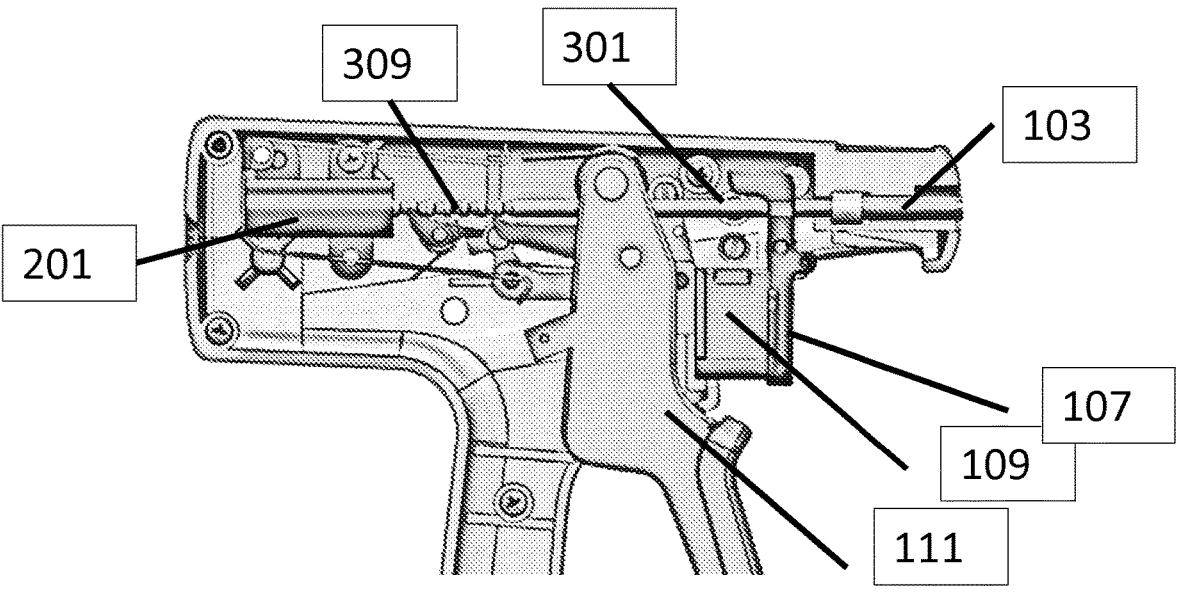
FIGS. 12a-12b show an example implant assembly inserted into the implant tool according to some embodiments.
Figure 12B:
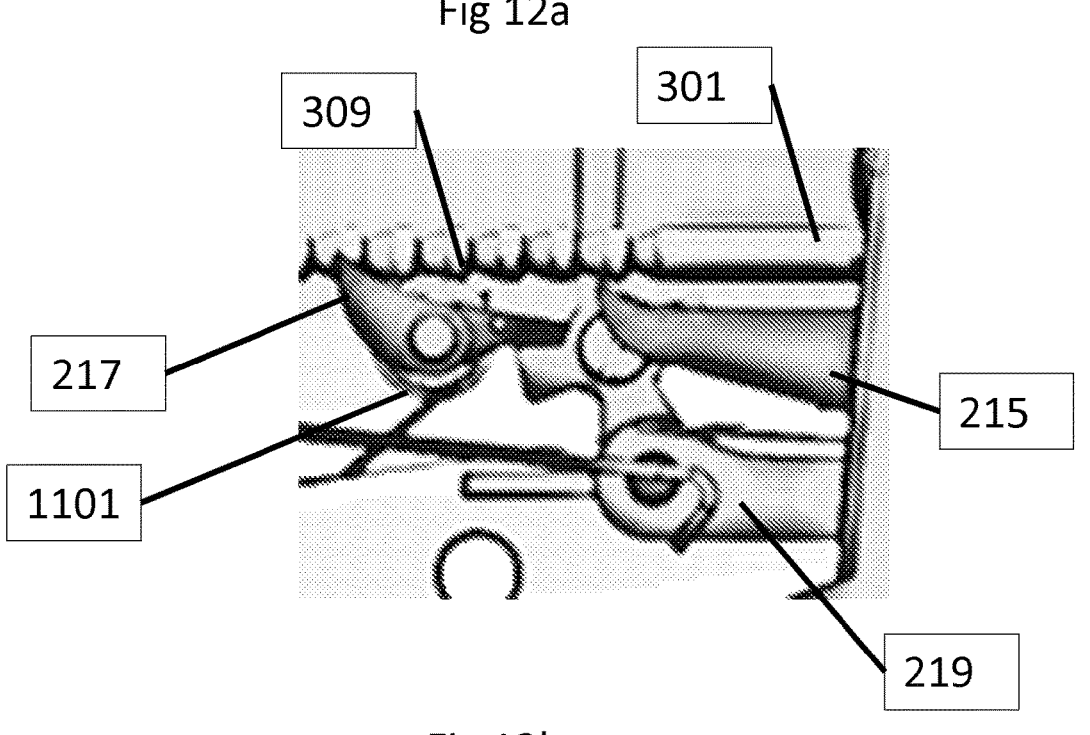

With respect to FIGS. 12a and 12b cross-sectional views of an example implant tool 101 is shown where the implant assembly 301 comprising the connection rod 303 has been inserted via the loading tube 103. The connection rod 303 as described herein comprises an interface 309 for coupling to the implant tool 101, in the form of grooves which co-operate with the first hook 215 and the second hook 217 and form a loading mechanism and specifically a locking or ratchet mechanism allowing the movement in an inwards direction only. Although in this example the loading mechanism is implemented by the use of hooks it would be understood that the term hook can define any suitable surface or profile enabling a hooking, gripping or catching of the implant assembly (or removal assembly). Similarly the term groove would be understood to mean any suitable co-operating surface or profile enabling the implant assembly to be hooked, gripped or caught.

In other words the interface 309 of the connection rod in some embodiments comprises a number of circular grooves which are configured to interface with the two pivotable hooks 215, 217 which are part of the implant tool mechanism. The grooves in combination with the pivotable or movable hooks form a ratchet mechanism which enables the implant tool to exert high pulling or tension forces to the tongue advancer.

In some embodiments the loading (and furthermore the locking or ratchet) mechanism comprising the retraction lever 111 and the first hook 215, the second (latching) hook 217 and the connection rod grooves are designed in such a shape that the two hooks slide along the rod in the loading (inwards) direction but block the movement of the rod in the opposite (outwards) or release direction. The second (latching) hook 217 has the functionality of always blocking the movement of the rod in the direction opposite the loading direction. In some embodiments a small spring 1101 load ensures that the second hook is biased to operate in one of the grooves. The first hook 215 as described herein is coupled or connected to the retraction lever 111. When the retraction lever 111 is operated, the first hook 215 is configured to engage one of the connection rod grooves and push the connection rod in the direction of loading. The ratio between the length of the retraction lever 111 and length of the first hook 215 results in the force transmission ratio of the mechanism. A smaller force on the retraction lever 111 can be translated to a larger force for pulling back the connection rod using the transmission ratio. After releasing the retraction lever 111 the second hook 217 engages the grooves to keep the connection rod in the new position while the first hook 215 moves along the rod and engages the next groove. From the new position the operation can be repeated until the connection rod is sufficiently loaded.

In some embodiments as described herein the first hook 215 can be replaced by a gear wheel which is gearing into a gear rack on the connection rod. The gear wheel can be operated by a hand wheel by the operator and replaces the retraction lever mechanism. In some embodiments the hook/groove combination can be replaced by a clutch/rod combination that relies on a friction coupling instead of a gear shape coupling.

Although the above describes a locking mechanism wherein the connection rod is able to be inserted but is locked from being released is shown herein with respect to a ratchet mechanism implemented by hooks or clutch and gear wheel systems it would be understood that in some embodiments any suitable locking mechanism can be employed.

The operation of inserting the implant assembly into the implant tool is shown in FIG. 18 by step 1715.

The tongue advancer is then retracted into the implant tool, for example by operating the retraction lever causing the fingers of the tongue advancer to straighten and pass completely inside the implant tool 101 loading tube 103. Thus at this stage the implant (or insertion) assembly comprising the tongue advancer and the connection rod has been fully inserted into the implant tool.

The operation of retracting the tongue advancer into the implant tool until the tongue advancer fingers are completely inside the implant tool tube is shown in FIG. 18 by step 1717.

The loaded implant tool can then in some embodiments be inserted into the implanted cannula part 3 which has kept the channel open. In some embodiments the coupling or connection of the implant tool 101 and the implanted cannula part 3 is felt by a latching mechanism within the implant tool 101 latching the cannula part 3.

The operation of inserting the loaded implant tool into the implanted cannula is shown in FIG. 18 by step 1719.

In some embodiments the operator checks the location of the implanted cannula by palpating the tongue with the hand inside the patient's mouth.

The operation of performing a "final" check of the position of the cannula is shown in FIG. 18 by step 1721.

In some embodiments the propulsion element such as the spring load element 201 of the implant tool 101 is charged with mechanical energy during the retraction of the implant assembly. The energy used to push or force the connection rod into the spring load element 201 can then be released in order to push or propel the implant along the loading tube. It would be understood that in some embodiments the propulsion element, such as for example the spring load element, can provide a force substantially in the range from 30-75 N to the connecting rod or removal sleeve and adaptor to propel it from the implant/removal tool. As described herein the propulsion element can be charged during loading, before loading or after loading. In other words a mechanism pre-charged relative to the operation of the release mechanism.

The procedure of operating a release mechanism and propelling the tongue advancer (or the connection rod with coupled tongue advancer) can be performed by lifting the safety cover or trigger guard 107 and pressing the trigger or release button 109. In some embodiments the trigger or release button 109 is configured to be coupled or connected to a hook release lever 219 which is configured to lift the first hook and the second hook from the connection rod grooves. The mechanical energy stored in the propulsion element such as the spring load propels or pushes the connection rod forward and the coupled tongue advancer out of the tool loading tube.

The operation of deploying the tongue advancer into the tongue is shown in FIG. 18 by step 1723.

It would be understood that the forced implantation of the tongue advancer as shown in some embodiments by use of propulsion element (spring load) has many advantages. The first of which is the ability to perform an accurate implantation as only a small amount of force (that of pressing the trigger/button) applied by the operator rather than physically pushing the implant. This enables an accurate implantation as relatively little force on the tongue is needed to be applied and as such the tongue is kept relatively still as compared to the range of motion caused while physical pushing the implant into the tongue. A further advantage is that the forced implantation of the tongue advancer by a spring load (or propulsion element which is charged) does not introduce any potential foreign matter as the implantation force means (the spring load element) remains within the implant tool as compared to gas implantation or other propulsive means which may escape the tool.

An additional advantage of the operations as described herein is where the implant may require to be repositioned. Where repositioning is necessary, for example when it is determined that the tongue advancer has not located itself in the desired location then the tongue advancer as part of the connection rod assembly is retracted by operating the retraction lever to operate the loading mechanism to load the connection rod assembly back into the implant tool.

This causes the fingers of the tongue advancer to be loaded (retracted) within the implant tool loading tube and permits the implant tool to be decoupled or disconnected from the implant cannula. Following the decoupling the implant tool can be removed allowing a recoupling or reconnection of the trocar tool into the cannula and the repetition of the steps of advancement of the trocar to tongue advancer deployment.

The operation of repositioning (an optional step) is shown in FIG. 18 by step 1725.

In some embodiments the implant tool 101 can comprise an ejection or implant counter and locking mechanism. The ejection or implant counter is configured to count the number of implantation and removal attempts. Furthermore the locking mechanism is configured to lock the implant tool after a determined number of implantation and removal attempts. For example the locking mechanism can in some embodiments be configured to lock the implant tool after determining three implantation and four removal attempts. The implant counter and locking mechanism can for example be used to prevent damage to a tongue advancer caused by being repeatedly implanted and removed.

In such a manner the combination of the tools employed according to some embodiments allows a simple repositioning operation.

When it is determined that the tongue advancer has been inserted correctly then the implant tool 101 can be separated from the implant cannula 3. For example the implant tool 101 cannula release button or lever 105 is activated unlatching the cannula 3 from the implant tool 101.

The separation of the implant tool 101 from the implant cannula 3 leaves the implant assembly 301 in position within the implant cannula 3.

The operation of removing the implant tool 101 is shown in FIG. 18 by step 1727.

The connection rod can in some embodiments be rotated (anti-clockwise) relative to the tongue advancer to unscrew the coupling or connection between the connection rod and the tongue advancer. It would be understood that in other embodiments, where the coupling is a clamping or other means, there can be a release of the clamping or other means. For example the removal of the implant tool can in some embodiments cause the clamp elements to open up and release the tongue advancer.

The implant cannula 3 can then in some embodiments be removed.

Furthermore the connection rod can be removed to expose the tongue advancer tether.

The operation of exposing the tongue advancer tether by removing implant cannula and the connection rod is shown in FIG. 18 by step 1729.

In some embodiments the operator can then re-glove using sterile gloves. This is because further palpation of the tongue is no longer necessary.

The operation of re-gloving is shown in FIG. 18 by step 1731.

In some embodiments the operator can then connect or couple the bone anchor tether with the tongue advancer tether. In some embodiments this is performed by forming a flat symmetrical knot between the bone anchor tether and the tongue advancer tether. However any other suitable fixation or coupling could be employed in some embodiments.

The operation of coupling or connecting the bone anchor tether with the tongue advancer tether is shown in FIG. 18 by step 1733.

In some embodiments appropriate positions for holes for bone screws are marked on the mandible, the holes are drilled into the mandible and, the bone anchor attached to the mandible by use of bone screws.

The attachment of the bone anchor to the mandible is shown in FIG. 18 by step 1735.

FIGS. 13a to 13e shows an example of adjustment tool suitable to be used in embodiments where the bone anchor comprises a spool mechanism. In the following examples the bone anchor comprises a spool mechanism. However it would be understood that in some embodiments the bone anchor does not comprise a spool mechanism and the adjustment can be made in another known manner. FIG. 13a shows the full tool assembly. It comprises a handle 90, a lock/unlock control section 92, an adjustment section 94 for controlling adjustment and an assembly of needles 96. This needle assembly 96 has at least two concentric parts, in the form of a smaller inner control shaft 98 which projects distally beyond the larger outer control shaft 100. They each terminate at a drive head.

The lock/unlock control section is shown in more detail in FIG. 13b. It controls the rotation of the inner (longer) needle part. For example, a counter clockwise step is used for unlocking, and a clockwise step back is used for locking. The lock knob 92 and lock/unlock central needle part 98 are rigidly connected.

The second, outer needle 100 is a control shaft that can be rotated independently. FIG. 13c shows the parts 94, 100 involved in tether line adjustment. The adjustment section is shown transparent to show that the inner hole of the adjustment knob and the outer diameter of the outer adjustment control shaft 100 connect to each other.

The components of the needle assembly 96 are shown in more detail in FIG. 13d. There is an outer sleeve 102 at the outside of the needle assembly 96 which can rotate freely over the outer control shaft 100. The outer sleeve which terminates set back from the distal end of the outer control shaft 100 and it can be fixed with respect to the adjustment section 94. It serves two purposes. The first is that it remains in a fixed position in the channel of operation to avoid damage and irritation along the created access path in the human body while doing the adjustment. This can be achieved either by fixing the outer sleeve to the adjustment section 94 or by allowing it to rotated freely, in which case it will be held rotationally still by contact with the patient. The second is that its distal end provides a stop; the distance over which the inner lock control shaft 98 and outer control shaft 100 can be pushed into the corresponding bone anchor components is limited, thus protecting these components from damage due to excess of pushing force.

FIG. 13e shows the tip of the needle assembly 96 in more detail. In this example, both the lock/unlock control shaft 98 and the outer control shaft 100 have an outer hexagonal shape. Their sizes match the hole dimensions of the corresponding bone anchor components. It can be seen from the two examples above that there are two rotating parts. The first can be the actual spool to wind tether, and the second can be the driver of a mechanism to block the spool. Both bodies can have the same axis of rotation, so that they have coaxial parts, and have non-circular holes for engagement with corresponding needle tips. The proximal one has a larger hole.

The tool head for this proximal body cannot penetrate into the distal hole. The smaller tool head for the distal body can rotate freely in the proximal body hole. The tool has coaxial shafts for engaging with the bone anchor. In one embodiment, the deeper slot (of the distal body) can be reached only by the needle part which is for locking the spool. This needle part is then free to rotate in the higher slot (of the proximal body). The adjustment needle part is bigger and matches the spool slot but cannot enter the lock slot. In principle the functions of locking and adjustment can also be interchanged so that the spooling control is deeper in the device and the locking is shallower in the device.

In the examples shown, a hexagonal drive head is at the end of each control shaft of the tool. Of course, this can be any other interlocking shape, including a screwdriver type head for the inner control shaft, and other polygons or more complicated bolt head designs. The openings in the spool and rotatable index locking part will be designed to correspond.

In some embodiments the adjustment tool and the lock tool is engaged into the lock interface of the bone anchor. This unlocks the bone anchor spool. The unlocking of the bone anchor is shown in FIG. 18 by step 1737.

In some embodiments the adjustment interface of the engaged adjustment tool is engaged into the adjustment interface of the bone anchor. The length of the tether can be adjusted as desired and slack removed from the bone and tongue advancer tethers. The operation of removing slack from the tethers is shown in FIG. 18 by step 1739.

The operator then in some embodiments engages the lock tool of the engaged adjustment tool into the lock interface of the bone anchor to lock the bone anchor spool.

The locking of the bone anchor is shown in FIG. 18 by step 1741.

In some embodiments and the operator then closes the original incision.

The closing of the incision is shown in FIG. 18 by step 1743.

In such a manner the implant stage is complete. The system, in other words the tethers between the tongue advancer and bone anchor are not stressed at implantation to enable the healing process. However following a sufficient healing time the adjustment stage can be performed where the implanted apparatus or devices can be adjusted by spooling tether into the bone anchor after the healing process is completed. This advances the tongue in the direction of the mandible and prevents the tongue from moving back and blocking the airway.

Figure 19:
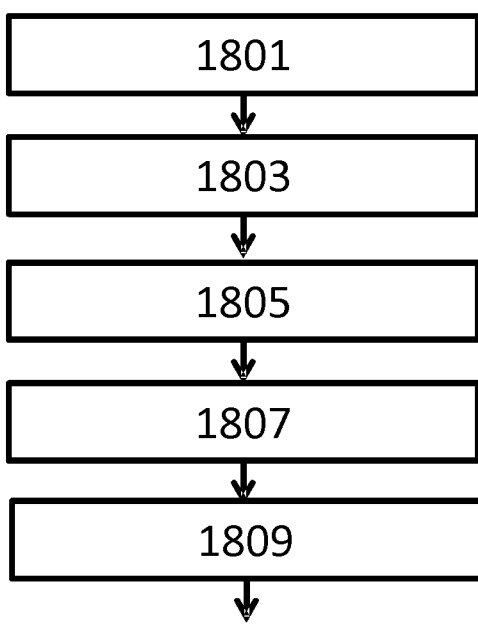
FIG. 19 shows a flow diagram of an example adjustment stage according to some embodiments.

The operation of adjustment stage can thus be summarised by the following steps as shown with respect to FIG. 19.

An incision is made directly over the bone anchor funnel (using a scalpel for example).

The operation of making an incision directly over the bone anchor funnel is shown in FIG. 19 by step 1801.

The lock tool of the adjustment tool is inserted into the lock interface of the bone anchor and the bone anchor unlocked using the adjustment tool.

The operation of engaging the lock tool and unlocking the bone anchor using the adjustment tool is shown in FIG. 19 by step 1803.

The adjustment tool is engaged in the in the adjustment interface of the bone anchor and is rotated to produce the desired length of tether.

The operation of engaging the adjustment tool and adjusting the length of the tether is shown in FIG. 19 by step 1805.

Once the tether has been adjusted to the desired length then the adjustment tool lock tool is engaged into the lock interface of the bone anchor and the bone anchor locked.

The operation of engaging the lock tool into the lock interface of the bone anchor and locking the bone anchor is shown in FIG. 19 by step 1807.

The operator then closes the incision ending the adjustment procedure.

The operation of closing the incision is shown in FIG. 19 by step 1809.

As discussed herein, in some embodiments, it is required to remove the bone anchor, tongue advancer and tether from the patient by minimally invasive surgery. The operations or steps with respect to the removal stage according to some embodiments are described with respect to FIG. 20.

The bone anchor is located on the patient's mandible.

Figure 20:
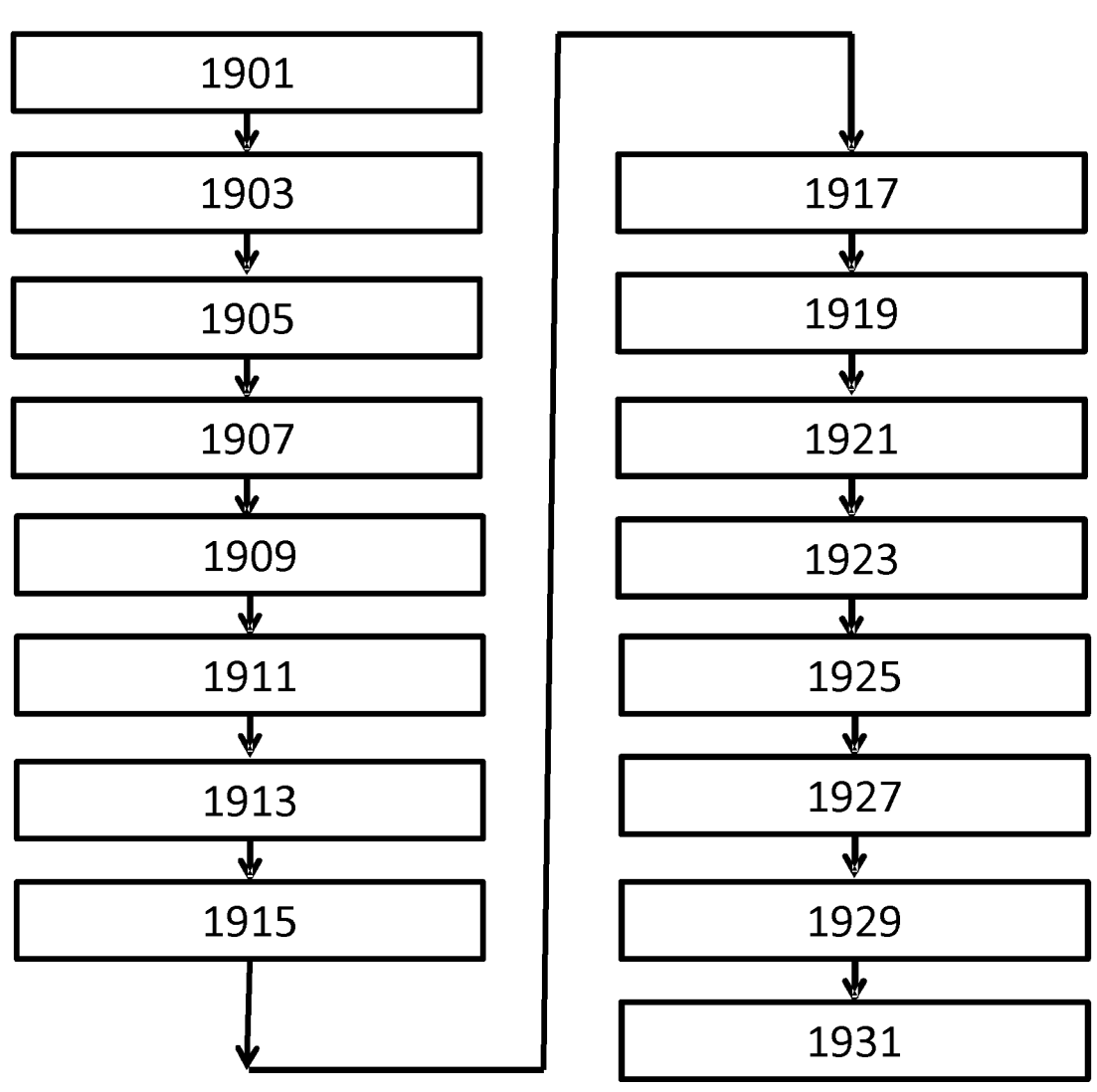
FIG. 20 shows a flow diagram of an example removal stage according to some embodiments.

The operation of locating the bone anchor is shown in FIG. 20 by step 1901.

An incision is then made into the skin a few millimetres away from the bridge of the bone anchor.

The operation of making a first or initial incision is shown in FIG. 20 by step 1903.

Using the adjustment tool, such as shown in FIGS. 13a to 13e, the lock tool engages the lock interface of the bone anchor and unlocks the bone anchor. For example by turning the lock/unlock part of the adjustment tool in a counterclockwise direction until a stop or slight click is heard. In some embodiments this can feel like a quarter turn.

The unlocking of the bone anchor is shown in FIG. 20 by step 1905.

The adjustment tool then unspools the bone anchor tether while applying a slight tension to the tether to facilitate the tether and square knot to exit the bone anchor housing. In some embodiments this can be about 2 cm after the knot has exited the bone anchor. It would be understood that in some embodiments where the tether begins to spool back up then the full length of the bone anchor tether has been exposed.

The operation of unspooling the bone anchor tether is shown in FIG. 20 by step 1907.

The bone anchor is then detached from the mandible by unscrewing the bone screws. In some embodiments this may involve clearing any bony overgrowth from the mandible plate of the bone anchor.

The operation of detaching the bone anchor from the mandible is shown in FIG. 20 by step 1909.

The bone anchor tether is then un-knotted from the tongue advancer tether or in some embodiments the bone anchor tether is cut to present the exposed loop of the tongue advancer tether. In some embodiments the tongue advancer tether loop can be exposed by using fingers however a blunt instrument can be used to assist this operation taking care not to damage the tether loop or where the tether loop is damaged to reconstruct a new loop suitable for hooking.

The operation of presenting the exposed loop of the tongue advancer tether is shown in FIG. 20 by step 1911.

Figure 14:
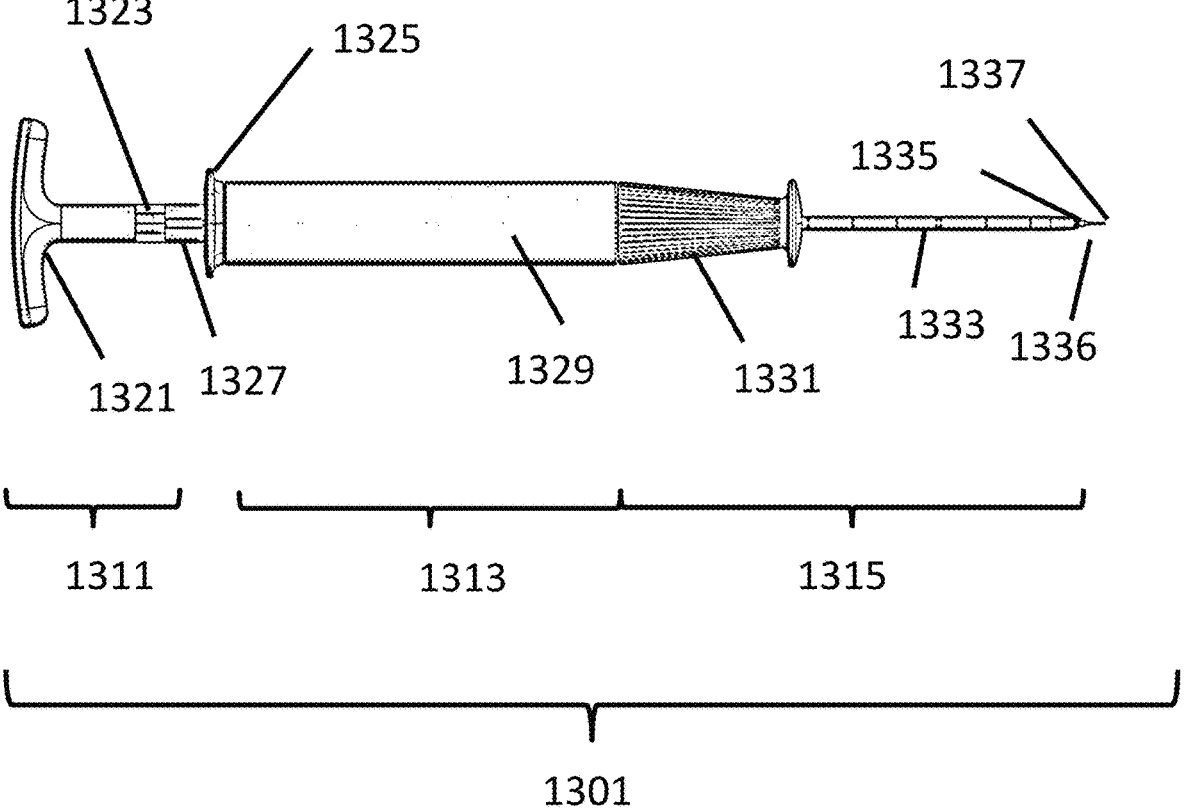
FIG. 14 shows an example connection tool according to some embodiments.

With respect to FIG. 14 an example connection tool is shown according to some embodiments. The connection tool 1301 can be considered to comprise four parts.

The first part in some embodiments is a separable or detachable removal cannula part 1315. The detachable removal cannula part may comprise the attachment knob or attachment rotator 1331 and the removal tube or removal cannula 1333. The removal tube or removal cannula 1333 in some embodiments can be considered to operate in a similar manner to the cannula part 3 of the trocar tool/implant tool operations in that it enables a stable channel to be formed. This stable channel is one through which the removal operations can be performed. In some embodiments therefore the removal tube 1333 is a hollow tube which can be manufactured from stainless or surgical grade steel or other suitable material. The attachment knob 1331 is in some embodiments a hollow tube which can either be attached to or be located around the removal tube 1333 and made from a suitable plastic material. In some embodiments the attachment knob 1331 is configured to have suitable shape or design to permit both rotational and pushing forces to be applied to it.

At least partially within the removal tube 1335 is located the removal sleeve or attachment sleeve (removal) 1335. The removal sleeve 1335 is configured to have at the distal end a coupling part suitable for coupling to the proximal end of the tongue advancer. For example in some embodiments the removal sleeve 1335 comprises a screw, clamp, a ball shaped coupling or connector (for coupling to a socket shaped coupling or connector on the tongue advancer), a socket shaped coupling or connector (for coupling to a ball shaped coupling or connector on the tongue advancer), or a gripping surface or profile or similar element for coupling to the tongue advancer. The removal sleeve 1335, in some embodiments, therefore comprises at the distal end a structure similar to that described with the connection rod type structure. The removal sleeve 1335 in some embodiments can furthermore comprise a proximal coupling part such as a screw thread or clamping elements for coupling with a removal adaptor (or ratchet part) comprising features similar to the connection rod circular grooves (or other suitable means for forming a coupling or connection with the removal tool). The removal sleeve 1335 when coupled to the tongue advancer and to the removal adaptor (ratchet part) 1334 can be considered to form a removal assembly. The removal assembly can be configured to retract the tongue advancer within the removal tool. Furthermore the removal assembly is therefore similar to the implant assembly comprising a coupling of the connection rod and the tongue advancer for retracting the tongue advancer within the implant tool.

The second part in some embodiments is the separable middle or body part 1313 comprising a floating knob or midsection grip 1329. The floating knob 1329 is a hollow tube within which a dissector body (which is part of a dissector assembly or a sliding assembly) 1327 can be located. The floating knob 1329 can be configured to be separably coupled to the proximal end of the attachment knob 1331 and be formed from a plastic or other material.

The third part in some embodiments is the dissector or sliding assembly. The dissector or sliding assembly in some embodiments comprises a series of hollow tube like structures which can be located at least partially within the floating knob 1329, the attachment knob 1331, the removal tube 1333 and the removal sleeve 1335. The sliding assembly in some embodiments comprises a dissector body 1325 and dissector 1336 which is located at least partially within the removal sleeve 1335. The dissector 1336 can in some embodiments be configured to have at the distal end a tip suitable for cutting tissue.

The sliding assembly can in some embodiments be formed of more than one part. For example the sliding assembly can comprise a proximal plastic part with a keying feature 1327 and keying base implemented within the dissector body 1325 suitable for rotationally locking (or unlocking) the sliding assembly to the floating knob 1329 and attachment knob 1331. Rotation of the attachment knob 1331 when the sliding assembly is rotationally locked allows the dissector 1336 with a sharpened edge for cutting tissue to rotate as the connection tool is advanced along the tether line into the patient.

In some embodiments the dissector body 1325 can be coupled or connected to the floating knob 1329 such that, when a positive connection between the removal sleeve 1335 and the tongue advancer is made, the dissector 1336 is pushed inwards (in a proximal direction relative to the removal sleeve) causing an indicator or flaring of the dissector body 1325 away from the floating knob 1329. Such embodiments therefore provide a clear indicator of a positive connection between the connection tool and the tongue advancer.

The fourth part of the connection tool in some embodiments is the tensioning assembly 1311. The tensioning assembly in some embodiments comprises the tensioner 1321 or tension handle, which is connected to a tension meter 1323, which in turn is coupled or connected to a detachable tension rod which is located at least partially within the sliding assembly and has at the distal end a tension hook 1337. Although the tension meter is connected to the tension hook by a detachable tension rod it would be understood that any suitable detachable coupling could be employed, such as a tension line or tube.

The tensioner 1321 can be any suitable means for applying tension to the tension rod and tension hook 1337, via the tension meter 1323. In the example shown in FIG. 14 the tensioner 1321 is a handle suitable for pulling and applying a force is a direction away from the body of the tool. However the tensioner 1321 can be implemented as one of:

an external retainer, a spooling spring, a linear spring, a mass or weight acting under gravity, a slider or a motor, such as a user controlled motor.

The tension meter 1323 can be any suitable force (tension) sensing or detecting means. For example in some embodiments the tension meter 1323 comprises at one end a body or window which is connected to one end (the tensioner 1321) and a visible indicator connected to the other end (the tension rod and tension hook 1337), wherein the body and the indicator are connected by a spring or resilient biasing force means configured such that when the tensioner 1321 applies a force and moves the body that the spring draws the visible indicator (various colour bars or blocks) along the window providing an indicator to the user the level of force/tension being applied by the tension hook 1337 to the tongue advancer tether line.

The tension meter 1323 can for example have three regions identifying the level of tension or force being applied. The first region which is displayed when the tension is first applied is an orange colour bar or block indicating a resting position or zero tension and further indicating when the tension is too low. The second region, a green colour bar or block, is displayed when the tension is correct. Thus at a desired tension the window displays the second region producing a fully green window. The third region, a red colour, is displayed such that when too much tension has been applied the window displays a red colour. It would be understood that ranges of tensions can vary according to the example implementation. For example a 'too low', 'desired' and 'too much' tension value can be based on the grade or type of tether line used. For example a 'too low' tension range (an orange colour bar is displayed) can be set for a range of values from 0-10 N. A 'desired' tension range (a green colour bar is displayed) can be set for a range of values from 5-25 N. A 'too much' tension range (a red colour bar is displayed) can be set for a range of values above 10 N.

Although an orange, green, red bar (or block) region colour example is shown it would be understood that any suitable colour, or display window configuration can be employed. Similarly although a linear display or tension meter is shown, it would be understood that a rotational meter can be employed in some embodiments. Furthermore in some embodiments the tension meter may be an arrow or similar pointer displaying a tension meter reading on a suitable scale.

The tension rod is located at least partially within the sliding assembly and has at the distal end a tension hook 1337. The tension rod can be configured with at least one detachable section such that the tensioner 1321 and tension meter 1323 can be detached from the tension hook 1337.

The tension hook 1337 can be any suitable material or design and is configured in embodiments to couple an exposed tongue advancer tether line into the connection tool and apply a suitable tension to the tether line as the sliding assembly moves towards the tongue advancer. Or in other words the tension hook 1337 and tongue advancer tether line can be pulled within the connection tool by the application of a pulling force on or by the tensioner. Although the examples herein describe the use of a tension hook 1337, it would be understood that the term hook defines any suitable connection or coupling, gripping or catching element, mechanism or means to couple or connect to the tongue advancer tether line.

The first operation with respect to the connection tool in some embodiments is to couple the connection tool, and in some embodiments the tension hook 1337, to the tongue advancer tether line. In some embodiments the connection tool is in a non-keyed mode or position. The connection tool tensioner 1321 is then pulled gently to fully seat the tongue advancer tether line loop in the hook.

The operation of hooking or seating the loop of the tongue advancer tether line within the connection tool tension hook is shown in FIG. 20 by step 1913.

The connection tool, and in some embodiments the connection tool tensioner 1321 is then pulled to apply a suitable tension on the tether line. This can for example be determined by the tension meter 1323. As described above the tension meter 1323 when operating in the suitable tension range displays a viewing window with a fully green colour block rather than displaying any orange (too little tension) or red (too much tension).

The operation of tensioning the tether to the required amount is shown in FIG. 20 by step 1915.

In some embodiments the location of the implanted tongue advancer is now determined. This can be performed for example by palpating the tongue to establish the location of the implanted tongue advancer.

The operation of locating the implanted tongue advancer is shown in FIG. 20 by step 1917.

The connection tool can then be advanced through the tissue, the connection tool being held approximately in alignment with the estimated orientation of the tongue advancer tether by gripping/rotating the floating knob 1329 and/or the attachment knob 1331 while applying tension to the tether line via the tensioner 1321 and therefore moving the sliding assembly over the tether. In some embodiments this can be continued until the tongue advancer has been reached. It would be understood that in some embodiments the tether line may be followed at an oblique angle.

Figure 15:
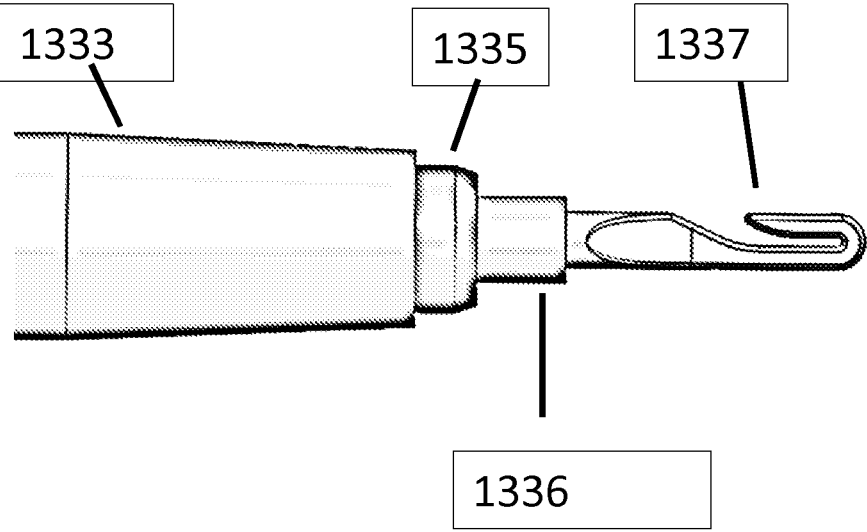
FIG. 15 shows a detail of a connection tool according to some embodiments.

With respect to FIG. 15 a detail of the end of the connector tool as shown in FIG. 14 is shown. In the example figure the removal tube 1333 is shown. Extending from within the removal tube is the removal sleeve 1335. The removal sleeve 1335 is configured to have at the distal end a coupling part suitable for coupling to the proximal end of the tongue advancer. For example in some embodiments the removal sleeve 1335 comprises a screw, clamp, a ball shaped coupling (for coupling to a socket shaped coupling on the tongue advancer), a socket shaped coupling (for coupling to a ball shaped coupling on the tongue advancer), or a gripping surface or profile for coupling to the tongue advancer. Furthermore extending from within the removal sleeve 1335 is the dissector 1336. The dissector 1336 comprises, as described herein, a tip configured to be suitable for cutting tissue. In other words the dissector comprises a sharpened or cutting edge. In order that when the tether line is followed at an oblique angle the tether line is not cut by the dissector 1336, in some embodiments the dissector comprises a flexible part or end configured to flex and prevent the tether line from contacting the dissector tip cutting edge. The flexible part or end can be manufactured from any suitable material. Furthermore extending from within the dissector 1336 is shown the tension hook 1337. The tension hook 1337 as described herein can be any suitable design suitable for coupling or connecting to the exposed tongue advancer tether line and applying a suitable tension to the tongue advancer tether line.

Figure 16:
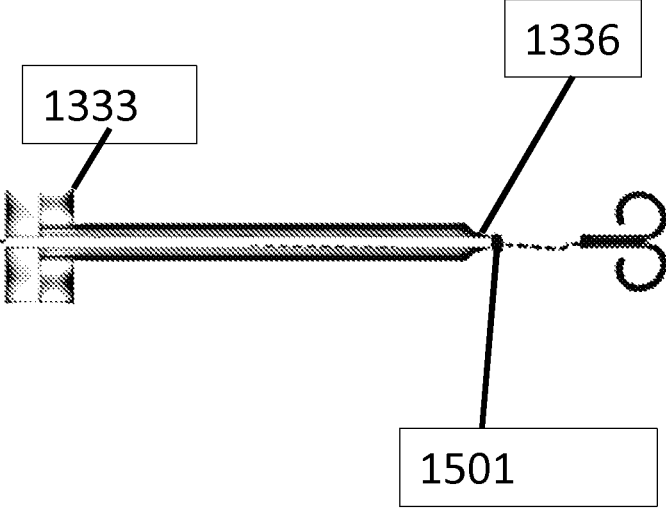
FIG. 16 shows a detail of a blunt dissector end according to some embodiments.

Furthermore with respect to FIG. 16 a further example of a suitable tether protection device is shown. In the example shown in FIG. 16 the dissector 1336 comprises a blunt dissector tip 1501 which in some embodiments can be located on the inside edge of the dissector tip and which is configured to separate the tether line and the cutting edge of the dissector where the tether line is followed at an oblique angle.

Where the connection tool is rotated to provide the dissecting or cutting force into the tissue it would be understood that in some embodiments the rotation is kept in a clockwise rotation where the coupling between the connection tool (and specifically the removal sleeve 1335) and tongue advancer is a screw coupling.

However it would be understood that the advancement can be performed in any suitable manner, such as, for example a wiggling motion.

The operation of advancing the cannula along the tether into the tongue while maintaining tension on the tether is shown in FIG. 20 by step 1919.

The cannula is advanced until a solid connection between the connection tool and tongue advancer is achieved.

In some embodiments the identification or confirmation of connection between the connection tool and the tongue advancer can be determined by feeling a movement of the tongue advancer within the tongue by a palpating hand.

Furthermore in some embodiments the identification or confirmation of contact between the connection tool (and specifically the removal sleeve) and the tongue advancer is determined by a disconnect between the dissector body 1325 or an interior body part and the floating knob 1329 as described previously.

The connection tool, in contact with the proximal end of the tongue advancer, can then be coupled to the tongue advancer by the coupling means of the removal sleeve and the tongue advancer. Thus for example in some embodiments the removal sleeve comprises a screw coupling and is configured to be rotated in a clockwise direction down the tether path and to be coupled to the proximal end of the tongue advancer. In some embodiments the removal sleeve experiences an increased resistance to rotation when solidly coupled to the tongue advancer caused by the tongue advancer exerting a resistive rotational force in response to the rotation of the removal sleeve.

The coupling of the connection tool and the tongue advancer is shown in FIG. 20 by step 1921.

In some embodiments once a solid contact between the removal sleeve 1335 and the tongue advancer has been achieved then the body 1313 of the connection tool can be separated from the detachable removal cannula part 1315 and the body of the connection tool moved away from the patient with the detachable removal cannula part 1315 left in place. For example the floating knob 1329 and the tensioning assembly 1311 can be separated from the detachable removal cannula part 1315. The floating knob 1329 and the tensioning assembly 1311 can then be moved away from the patient.

This can be achieved in some embodiments by the features in front of the tension meter window, in other words keying the slider assembly and body of the connection tool until a hard stop of the tensioner handle is reached.

In some embodiments therefore the removal sleeve 1335 is retained within the removal tube 1333 when the floating knob 1329 and the tensioning assembly 1311 is separated from the detachable removal cannula part 1315 and the body of the connection tool comprising the floating knob 1329 and the tensioning assembly 1311 is moved away from the patient. Furthermore the tension rod detachable section is detached such that the tensioner 1321 and tension meter 1323 can be detached from the tension hook 1337 thus enabling the tensioning assembly 1311 to be moved while the tension hook and tether line is handled separately.

Furthermore in such embodiments following the separation of the connection tool body from the detachable cannula part 1315 (including the removal sleeve 1335), the removal adaptor (ratchet part) is coupled to the proximal end of the removal sleeve 1335 to form a removal assembly. In some embodiments it would be understood that the removal sleeve 1335 comprises an integral removal adaptor 1334 located or coupled at the proximal end of the removal sleeve 1335. The removal assembly in some embodiments therefore comprising the removal adaptor (or ratchet part) coupled to the removal sleeve 1335 at the proximal end of the removal sleeve 1335, and the removal sleeve 1335 at the distal end of the removal sleeve coupled to the tongue advancer.

The separation of the connection tool into the detachable cannula part 1315 (including the removal assembly and tongue advancer) and the connection tool body (including the tensioner 1321 and floating knob 1329 and the creation of a removal assembly is shown in FIG. 20 by step 1923.

Figure 17:
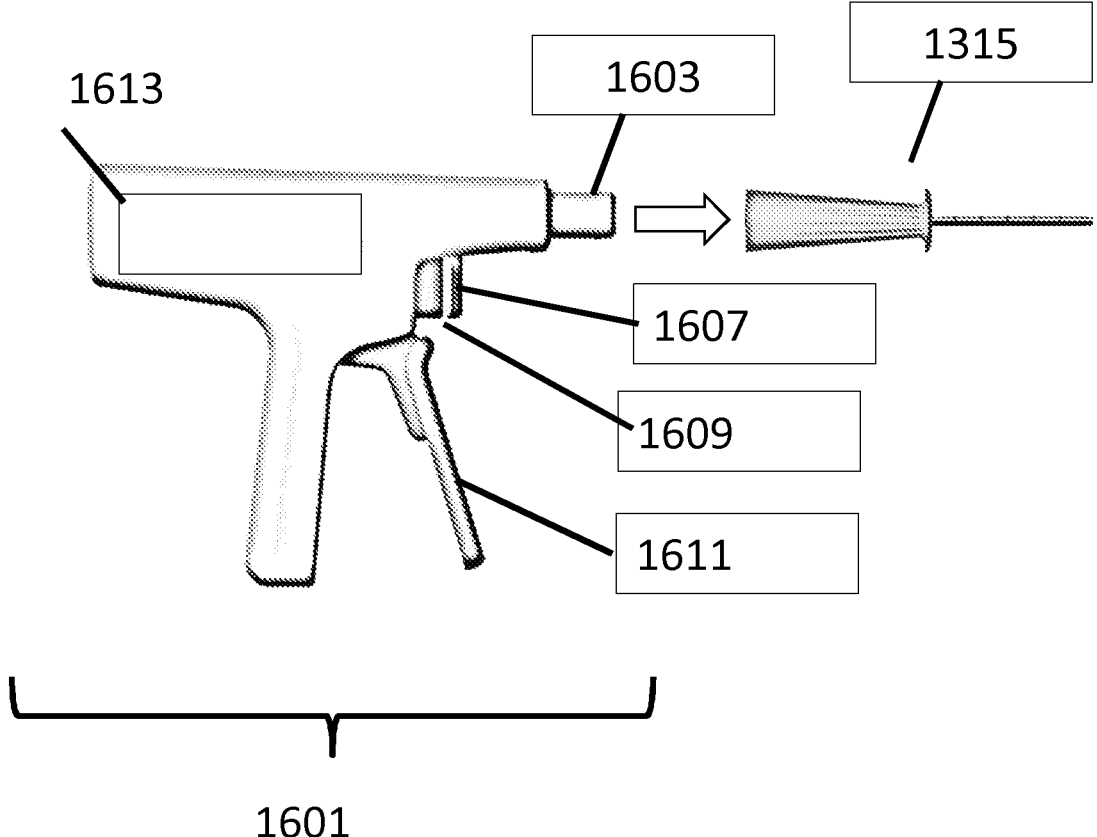
FIG. 17 show an example removal tool according to some embodiments.

With respect to FIG. 17 an example removal tool 1601 is shown. The removal tool 1601 as shown in FIG. 17 comprises a body 1613 incorporating a handle part. The body 1613 can be manufactured or formed from any suitable material, for example from an injection moulded plastic. The body 1613 can in some embodiments have other components mounted from it. For example as shown in FIG. 17 the body 1613 is coupled or connected via an internal pivot point to a retraction lever 1611. The retraction lever 1611 in some embodiments as shown in FIG. 17 is configured to be operable by the use of at least one finger when the operator of the tool is holding the removal tool and can be formed from a moulded plastic part. The body 1613 can in some embodiments be further coupled to a safety lever or cover 1607 which is pivoted at a second pivot point within the body 1613 and is configured to cover or prevent the accidental pressing of a release button or trigger lever 1609. The body 1613 can in some embodiments be further coupled or connected to a removal assembly release button or trigger 1609.

The body 1613 can in some embodiments further comprise a coupling and/or latching section 1603 suitable for receiving the detachable removal cannula part 1315. This can for example be an axis-symmetrical or axis-directional slot within the distal end of the body 1613. Furthermore the latching section can for example be implemented by a latching mechanism such as a port key feature with a profiled end configured to fit an associated profile on a detachable removal cannula part 1315 when inserted onto the removal tool body 1613. The body 1613 can in some embodiments comprise a release or cannula release button or suitable latching release mechanism suitable for allowing the decoupling or disconnection between the removal tool 1601 and the detachable removal cannula part 1315.

The body 1613 in some embodiments comprises an internal loading tube or hollow. The internal loading tube or hollow configured to receive the removal assembly and at least the removal adaptor located inside and extending at least partially out of the removal tube 1333 in a proximal direction when the detachable removal cannula part 1315 is attached to the body of the removal tool 1601. The internal loading tube or hollow within the body 1613 can in some embodiments be configured to receive the proximal end of the removal tube 1333.

It would be understood that in some embodiments the removal tool comprises features similar to the implant tool with respect to a loading mechanism configured to load a removal assembly comprising the tongue advancer and, a propulsion element configured to be charged during the loading of the removal assembly and a release mechanism (implemented in some embodiments by the button release or trigger mechanism) configured to release the removal assembly comprising the tongue advancer. For example in some embodiments the removal tool 1601 comprises a loading mechanism comprising a first hook coupled to the retraction lever mechanism and a second hook which are both mounted such that they can pivot about respective points and hook or trap a ratchet groove feature on the removal assembly (and specifically the removal adaptor or ratchet part) such that the proximal end of the removal assembly can move in one direction, an inwards direction, but is trapped and prevented from moving in an outwards direction. The first hook is coupled or connected to the retraction lever mechanism such that, as the retraction lever is pulled towards the body of the removal tool, the first hook moves in an inwards direction relative to the body 1613. Furthermore the retraction mechanism comprises a propulsion element such as a biasing or spring load, which is charged on loading or retraction of the removal assembly into the removal tool. The propulsion element can, when the hooks are moved away from the grooves of the removal assembly, be configured to push or eject the removal assembly out of the removal tool. For example the hooks can be moved from the grooves of the removal assembly by a release or trigger mechanism actuated following pressing the release button or trigger lever 1609. The release button can for example be coupled to a suitable release mechanism to move the hooks away from the removal assembly and therefore disengage the hooks from the circular grooves.

Once again it would be understood that the term hook as used herein can define any suitable surface or profile enabling a hooking, gripping or catching of the removal assembly. Similarly it would be understood that any other suitable locking, or ratchet mechanism can be employed which in combination with the removal assembly forms a suitable ratchet or locking mechanism permitting in a first or loading mode the removal assembly to be loaded into the removal tool in a manner similar to that described with respect to the implant tool. For example in some embodiments the removal tool comprises a suitable gearwheel to operate on the removal assembly. Similarly in some embodiments the removal tool comprises a suitable clutch mechanism using friction coupling to the removal assembly (which has an associated friction surface formed by suitable means).

The insertion of the removal tool 1601 into the detachable removal cannula part 1315 therefore causes the removal assembly and specifically the removal adaptor located at least partially within the removal tube to interface with the levers within the removal tool in a similar manner to loading the connection rod into the implant tool as described herein. In other words the removal adaptor and the removal sleeve in combination can be seen to form a connection rod. Similarly in some embodiments the connection rod such as shown with respect to the insert tool can comprise an insert or removal sleeve part which is configured to be coupled at a distal end to the tongue advancer, and to be coupled at a proximal end to an insert or removal adaptor. The insert or removal adaptor is further configured to be coupled at a distal end to the insert or removal sleeve and at a proximal end to the insert or removal tool respectively. In some embodiments the insert or removal adaptors are interchangeable and similarly in some embodiments the insert or removal sleeves are interchangeable.

The operation of coupling the removal tool to the removal assembly is shown in FIG. 20 by step 1925.

The removal tool can then be operated, in other words the retraction lever 1611 is operated until the tongue advancer is completely drawn into the removal tube 1333 by the removal assembly being pulled into the removal tool. In some embodiments the removal tool comprises a propulsion element such as a load spring. However any suitable propulsion element can be employed. Furthermore although the propulsion element in some embodiments can be configured to be charged during the loading of the removal assembly it would be understood that the propulsion element can be charged at some point prior to the propelling of the removal assembly.

In some embodiments of the removal of the tongue advancer is confirmed by palpating the tongue.

Following the confirmation of the retraction of the tongue advancer into the removal tool the removal tool and attached detachable removal cannula part is removed from the patient.

The operation of retracting the tongue advancer and removal of the device assembly from the body is shown in FIG. 20 by step 1927.

In some embodiments the removal tool 1601 is then directed at a suitable return container and the removal tool propulsion element (spring load) released by operating the safety lever 1607 and pressing the release button 1609 to propel the removal sleeve as part of the removal assembly further comprising the tongue advancer into the suitable return container.

The container can for example contain a foam material configured to receive the fingers of the tongue advancer and enabling the decoupling or disconnection of the tongue advancer (for example by unscrewing the tongue advancer). The removed tongue advancer can then be examined to determine whether it has been completely removed.

The operation of the checking the explanted tongue advancer is shown in FIG. 20 by step 1929.

The incision can then be closed having determined that the explanted tongue advancer is complete and has not experienced mechanical failure.

The operation of closing the incision is shown in FIG. 20 by step 1931.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A connection rod for a tongue manipulation device system, the connection rod comprising:

an elongate body extending between a proximal end and a distal end, the proximal end terminating in a tapered portion that tapers away from the distal end and is structured to be selectively disposed in an opening of an implant tool or a removal tool;

a first coupling part configured to couple the distal end of the connection rod to a tongue advancer; and a second coupling part configured to couple the proximal end of the connection rod to the implant tool or the removal tool, wherein the connection rod is configured to transmit a tension or pulling force from the implant tool or the removal tool to the tongue advancer such that the tongue advancer is configured to be retracted within the implant tool or removal tool respectively, and wherein the connection rod is at least partially hollow and configured to receive the tongue advancer, and a tongue advancer tether attached to the tongue advancer, at least partially within itself.

2. The connection rod as claimed in claim 1, wherein the first coupling part comprises a screw thread configured to couple to an associated tongue advancer screw thread.

3. The connection rod as claimed in claim 2, wherein the screw thread is one of:

an internal screw thread; or an external screw thread.

4. The connection rod as claimed in claim 2, wherein the screw thread is a partially executed screw thread.

5. The connection rod as claimed in claim 1, wherein the first coupling part comprises a clamp configured to clamp to the tongue advancer.

6. The connection rod as claimed in claim 5, wherein the clamp comprises at least one clamping element comprising a clamping profiled inner surface element extending radially inward that is configured to clamp the tongue advancer.

7. The connection rod as claimed in claim 6, wherein the connection rod is configured to be located within a hollow tube with a profiled inner surface such that as the hollow tube is moved in a distal direction over the connection rod, the profiled inner surface moves the clamping profiled inner surface element to clamp on a tongue advancer groove.

8. The connection rod as claimed in claim 5, wherein the clamp comprises a protrusion configured to contact a tongue advancer proximal end when the clamp is located in a position to clamp the tongue advancer.

9. The connection rod as claimed in claim 1, further comprising:

a removal sleeve comprising the first coupling part configured to couple the distal end of the connection rod to the tongue advancer; and a removal adaptor comprising the second coupling part configured to couple the proximal end of the connection rod to the removal tool, wherein a proximal end of the removal sleeve is coupled to a distal end of the removal adaptor to form the connection rod.

10. The connection rod as claimed in claim 1, wherein the second coupling part comprises at least one of:

a plurality of profiled grooves configured to interact with at least one hook or gearwheel to provide a ratchet mechanism for providing a tension or pulling force from the implant tool; and/or a friction surface configured to interact with at least one clutch or gearwheel to provide a ratchet mechanism for providing a tension or pulling force from the implant tool.

11. A tongue advancer implant assembly or a tongue advancer removal assembly for insertion into an implant tool or removal tool, the implant assembly or removal assembly comprising:

a connection rod comprising:

an elongate body extending between a proximal end and a distal end, the proximal end terminating in a tapered portion that tapers away from the distal end and is structured to be selectively disposed in an opening of the implant tool or the removal tool;

a first coupling part configured to couple the distal end of the connection rod to a tongue advancer; and a second coupling part configured to couple the proximal end of the connection rod to the implant tool or the removal tool, wherein:

the connection rod is configured to transmit a tension or pulling force from the implant tool or the removal tool directly to the tongue advancer such that the tongue advancer is configured to be retracted within the implant tool or removal tool respectively, and the connection rod is at least partially hollow and configured to receive the tongue advancer, and a tongue advancer tether attached to the tongue advancer, at least partially within itself; and a tongue advancer comprising:

a connection rod coupling coupling the tongue advancer to the distal end of the connection rod, and at least one tongue advancer finger configured to be deployed by unfolding, to locate the tongue advancer.

12. The tongue advancer implant assembly or the tongue advancer removal assembly as claimed in claim 11 wherein the connection rod coupling of the tongue advancer comprises at least one of:

a screw thread coupling the tongue advancer to the connection rod by a connection rod screw thread;

a groove coupling the tongue advancer to the connection rod by a connection rod clamping element;

a ball-shaped proximal end coupling the tongue advancer to the connection rod by a connection rod clamping element.

13. A connection rod for a tongue manipulation device system, the connection rod comprising:

an elongate body extending between a proximal end and a distal end, the proximal end terminating in a tapered portion that tapers away from the distal end and is structured to be selectively disposed in an opening of an implant tool or a removal tool;

a first coupling part configured to directly couple the distal end of the connection rod to a tongue advancer; and a second coupling part configured to couple the proximal end of the connection rod to an implant tool or a removal tool, wherein the second coupling part comprises a friction surface configured to be gripped within the implant tool by a suitable friction wheel that prevents the connection rod from exiting or leaving the implant tool via only frictional forces and provides a ratchet mechanism for providing a tension or pulling force from the implant tool, wherein the connection rod is configured to transmit a tension or pulling force from the implant tool or the removal tool to the tongue advancer such that the tongue advancer is configured to be retracted within the implant tool or removal tool respectively, and wherein the connection rod is at least partially hollow and configured to receive the tongue advancer, and a tongue advancer tether attached to the tongue advancer, at least partially within itself.

14. The connection rod as claimed in claim 13, wherein the first coupling part comprises a screw thread configured to couple to an associated tongue advancer screw thread.

15. The connection rod as claimed in claim 14, wherein the screw thread is one of:

an internal screw thread; or an external screw thread.

16. The connection rod as claimed in claim 14, wherein the screw thread is a partially executed screw thread.

17. The connection rod as claimed in claim 13, wherein the first coupling part comprises a clamp configured to clamp to the tongue advancer.

18. The connection rod as claimed in claim 17, wherein the clamp comprises at least one clamping element comprising a clamping profiled inner surface element configured to clamp the tongue advancer.

19. The connection rod as claimed in claim 18, wherein the connection rod configured to be located within a hollow tube with a profiled inner surface such that as the hollow tube is moved in a distal direction over the connection rod, the profiled inner surface moves the clamping profiled inner surface element to clamp on a tongue advancer groove.

20. The connection rod as claimed in claim 17, wherein the clamp comprises a protrusion configured to contact a tongue advancer proximal end when the clamp is located in a position to clamp the tongue advancer.

21. The connection rod as claimed in claim 13, further comprising:

a removal sleeve comprising the first coupling part configured to couple the distal end of the connection rod to the tongue advancer; and a removal adaptor comprising the second coupling part configured to couple the proximal end of the connection rod to the removal tool, wherein a proximal end of the removal sleeve is coupled to a distal end of the removal adaptor to form the connection rod.

* * * * *